United States Patent
Sohn et al.

(10) Patent No.: US 12,246,082 B2
(45) Date of Patent: Mar. 11, 2025

(54) EFFICIENT SUNSCREEN COMPOSITIONS WITH DIETHYLAMINO HYDROXYBENZOYL HEXYL BENZOATE AND BUTYL METHOXYDIBENZOYLMETHANE FREE OF OCTOCRYLENE

(71) Applicant: BASF SE, Ludwigshafen am Rhein (DE)

(72) Inventors: Myriam Sohn, Grenzach-Wyhlen (DE); Stanislaw Krus, Grenzach-Wyhlen (DE); Marcel Schnyder, Grenzach-Wyhlen (DE); Stephanie Acker, Grenzach-Wyhlen (DE)

(73) Assignee: BASF SE, Ludwigshafen am Rhein (DE)

( * ) Notice: Subject to any disclaimer, the term of this patent is extended or adjusted under 35 U.S.C. 154(b) by 689 days.

(21) Appl. No.: 17/439,631

(22) PCT Filed: Mar. 13, 2020

(86) PCT No.: PCT/EP2020/056917
§ 371 (c)(1),
(2) Date: Sep. 15, 2021

(87) PCT Pub. No.: WO2020/187767
PCT Pub. Date: Sep. 24, 2020

(65) Prior Publication Data
US 2022/0151898 A1 May 19, 2022

(30) Foreign Application Priority Data
Mar. 15, 2019 (EP) .................................... 19163177

(51) Int. Cl.
*A61K 8/49* (2006.01)
*A61K 8/35* (2006.01)
*A61K 8/44* (2006.01)
*A61Q 17/00* (2006.01)
*A61Q 17/04* (2006.01)

(52) U.S. Cl.
CPC .............. *A61K 8/4966* (2013.01); *A61K 8/35* (2013.01); *A61K 8/445* (2013.01); *A61Q 17/00* (2013.01); *A61Q 17/04* (2013.01); *A61K 2800/30* (2013.01); *A61K 2800/5922* (2013.01)

(58) Field of Classification Search
CPC ........ A61K 8/4966; A61K 8/35; A61K 8/445; A61K 2800/30; A61K 2800/5922; A61K 8/415; A61Q 17/00; A61Q 17/04
See application file for complete search history.

(56) References Cited

U.S. PATENT DOCUMENTS

| | | |
|---|---|---|
| 2005/0008587 A1 | 1/2005 | Schulz et al. |
| 2012/0128611 A1 | 5/2012 | Grumelard et al. |
| 2017/0128357 A1* | 5/2017 | Brillouet ................ A61Q 19/00 |

FOREIGN PATENT DOCUMENTS

| | | |
|---|---|---|
| CN | 102470081 A | 5/2012 |
| DE | 102013203559 A1 | 9/2014 |
| EP | 2092928 A1 | 8/2009 |
| EP | 2781211 A1 | 9/2014 |
| EP | 2837407 A2 | 2/2015 |
| EP | 3093006 A1 | 11/2016 |
| EP | 3093007 A1 | 11/2016 |
| EP | 3093008 A1 | 11/2016 |
| EP | 3195853 A1 | 7/2017 |
| EP | 3351236 A1 | 7/2018 |
| WO | 2011/003774 A2 | 1/2011 |

OTHER PUBLICATIONS

International Search Report and Written Opinion received for PCT Patent Application No. PCT/EP2020/056917, mailed on Jun. 9, 2020, 12 pages.
International Preliminary Report on Patentability received for PCT Patent Application No. PCT/EP2020/056917, mailed on Sep. 30, 2021, 10 pages.

* cited by examiner

Primary Examiner — Robert A Wax
Assistant Examiner — Quanglong N Truong
(74) Attorney, Agent, or Firm — Faegre Drinker Biddle & Reath LLP

(57) ABSTRACT

The present invention relates to sunscreen or daily care composition comprising (i) hexyl 2-[4-(diethylamino)-2-hydroxybenzoyl]benzoate (INCI diethylamino hydroxybenzoyl hexyl benzoate); and (ii) 1-(4-(1,1-dimethylethyl)phenyl)-3-(4-methoxyphenyl)propane-1,3-dione (INCI butyl methoxydibenzoylmethane); and (iii) 2,4-bis-{[4-(2-ethylhexyoxy)-2-hydroxy]-pheny}-6-(4-methoxypheny)-1,3,5 triazine (INCI bis-ethylhexyloxyphenol methoxyphenyl triazine); and (iv) 4,4',4"-(1,3,5-triazine-2,4,6-triyltriimino) tris-benzoic acid-tris(2-ethylhexyl)ester (INCI ethylhexyl triazone) and/or 4, 4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethyl-hexyl-butamidotriazone); and (v) at least one organic particulate UV filter, wherein the composition is free of ethylhexyl-2-cyano-3, 3-diphenyl-acrylate (INCI octocrylene), 2-ethylhexyl-(2E)-3-(4-methoxyphenyl) acrylate (INCI ethylhexyl methoxy cinnamate) and pp benzylidene malonates, and wherein the composition comprises diethylamino hydroxybenzoyl hexylbenzoate and butyl methoxydibenzoylmethane in a ratio of larger or equal to 0.8. Furthermore, the present invention relates to the use of said composition for the administration to sensitive skin. In addition, the present invention relates to the use of said composition to reduce sand adhesion after application of the composition on the skin.

20 Claims, No Drawings

EFFICIENT SUNSCREEN COMPOSITIONS WITH DIETHYLAMINO HYDROXYBENZOYL HEXYL BENZOATE AND BUTYL METHOXYDIBENZOYLMETHANE FREE OF OCTOCRYLENE

CROSS-REFERENCE TO RELATED APPLICATIONS

This application is a national stage application (under 35 U.S.C. § 371) of PCT/EP2020/056917, filed Mar. 13, 2020 which claims benefit of European Application No. 19163177.9, filed Mar. 15, 2019, both of which are incorporated herein by reference in their entirety.

The present invention relates to sunscreen or daily care compositions comprising diethylamino hydroxybenzoyl hexyl benzoate, butyl methoxydibenzoylmethane, bis-ethylhexyloxyphenol methoxyphenyl triazine, ethylhexyl triazone and/or diethylhexyl-butamidotriazone, wherein the composition is free of octocrylene and ethylhexyl methoxy cinnamate and wherein the composition comprises diethylamino hydroxybenzoyl hexyl benzoate and butyl methoxydibenzoylmethane in a ratio of larger or equal to 0.8. The present invention relates to the use of said composition to reduce sand adhesion after application of the composition on the skin. Furthermore, the present invention relates to the use of said composition for the administration to sensitive skin.

UV radiation causes harmful effects on the human skin. Beside the acute effect of sunburn of the skin, UV radiation is also known to increase the risk of skin cancer. Furthermore, long time exposure to UV-A and UV-B light can cause phototoxic and photo allergenic reactions on the skin and can accelerate skin aging.

To protect the human skin from UV radiation, various sun protecting UV filters (also referred to as UV absorbers) exist including UV-A filter, UV-B filter and broadband filters. These filters are added to sunscreen or cosmetic compositions. The UV filters are either organic or inorganic, particulate or non-particulate compounds, of which all have a high absorption efficacy in the UV-light range. In general, UV light can be divided into UV-A radiation and UV-B radiation. Depending on the position of the absorption maxima, UV-filters are divided into UV-A and UV-B filters. In case an UV-filter absorbs both, UV-A and UV-B light, it is referred to as a broadband absorber.

Since 2006, the EU commission has recommended that all sunscreen or cosmetic compositions should have an UV-A protection factor, which is at least one third of the labelled sun protection factor (SPF), wherein the sun protection factor refers mainly to the UV-B protection.

However, the UV filters known in the prior art, which are used in sunscreen or cosmetic compositions have certain disadvantages. A lot of sunscreen or cosmetic compositions contain UV filter, which are frequently under discussion due to their health and environmental concern, although they are approved for being used in sunscreen or cosmetic compositions. UV filter under discussion are for example octocrylene, homosalate, ethylhexyl methoxy cinnamate, 4-methylbenzylidene camphor, benzophenone-3 or ethylhexyl salicylate. Therefore, there is a need for sunscreen or cosmetic compositions of the daily use, which are efficient for sun protection but free of UV filter under discussion.

EP 2 837 407 A2 discloses odor stable, octocrylene free cosmetic compositions comprising one or more UV filter selected from triazine derivatives, titanium dioxide, butyl methoxydibenzoylmethane and/or diethylamino hydroxybenzoyl hexyl benzoate, wherein the composition is free of ethylhexyl salicylate, octocrylene, homomenthylsalicylate and ethylhexyl methoxy cinnamate.

EP 3 093 008 A1 refers to a sunscreen composition which is free of octocrylene, comprising diethylamino hydroxybenzoyl hexyl benzoate, phenylbenzimidazole sulfonic acid, and one or more salicylates selected from ethylhexyl salicylate and homosalate.

EP 3 093 007 A1 discloses a cosmetic composition comprising a UV filter combination of diethylamino hydroxybenzoyl hexyl benzoate, ethylhexyl triazone and one or more salicylates selected from ethylhexyl salicylate and homosalate, wherein the composition may further be free of oxybenzone, octocrylene and 4-methylbenzylidene camphor.

EP 3 093 006 relates to an alcohol containing, octocrylene free sunscreen composition. The cosmetic composition comprises an UV filter combination of diethylamino hydroxybenzoyl hexyl benzoate, ethylhexyl triazone, and bis-ethylhexylphenol methoxyphenyl triazine, wherein the composition comprises one or more alcohols.

EP 3 195 853 A1 discloses an octocrylene free sunscreen composition, wherein the cosmetic composition comprises an UV filter combination of diethylamino hydroxybenzoyl hexyl benzoate, diethyl butamido triazone and ethylhexyl triazone.

EP 3 351 236 A1 relates to a cosmetic composition comprising a UV filter combination of diethylamino hydroxybenzoyl hexyl benzoate, butyl methoxydibenzoylmethane and polyglycerol fatty acid esters, wherein the composition is free of 4-methylbenzylidene camphor, oxybenzone, ethylhexyl methoxycinnamate, isoamyl p-methoxycinnamate and octocrylene.

US 2012/0128611 describes cosmetic compositions comprising specific benzylidene malonates as a UV filter combined with another UV filter selected from a specific group. In particular, US 2012/0128611 discloses said UV filter combination for the protection of human and animal hair and skin against UV radiation.

Therefore, it has been an object of the present invention to provide efficient sunscreen or daily care compositions. It has been another object of the present invention to provide efficient sunscreen or daily care compositions having an improved performance meeting the current consumer compliance. In this connection, it has been another object of the present invention to provide sunscreen or daily care compositions, which are free of certain UV filter under discussion, i.e. octocrylene and ethylhexyl methoxy cinnamate. It has been another object of the present invention to provide a sunscreen or daily care composition, which is suitable for use in sunscreen or daily care products in order to be administered to sensitive skin. It has been another object of the present invention to provide a sunscreen or daily care composition, which is suitable for use in sunscreen or daily care compositions in order to reduce sand adhesion on the skin. A further object of the present invention is to provide sunscreen or daily care compositions, which show a bright color.

It has surprisingly been found that at least one of these objects can be achieved by the sunscreen or daily care composition according to the present invention. In particular, the inventors of the present application found that the sunscreen or daily care composition according to the present invention provides an efficient UVA and UVB protection, nevertheless the composition is free of certain UV filter under discussion, i.e. octocrylene and ethylhexyl methoxy cinnamate. Furthermore, it has surprisingly been found by the inventors of the present application that the sunscreen or daily care composition according to the present invention is photo stable, applicable to sensitive skin and meets the consumer conveniences such as a pleasant bright color and reduced sand adhesion after application on the skin.

Thus, according to one embodiment, the present invention relates to a sunscreen or daily care composition comprising
(i) hexyl 2-[4-(diethylamino)-2-hydroxybenzoyl]benzoate (INCI diethylamino hydroxybenzoyl hexyl benzoate); and
(ii) 1-(4-(1,1-dimethylethyl)phenyl)-3-(4-methoxyphenyl)propane-1,3-dione (INCI butyl methoxydibenzoylmethane); and
(iii) 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine); and
(iv) 4,4',4''-(1,3,5-triazine-2,4,6-triyltriimino)tris-benzoic acid-tris(2-ethylhexyl)ester (INCI ethylhexyl triazone) and/or 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone); and
(v) at least one organic particulate UV filter,
wherein the composition is free of ethylhexyl-2-cyano-3,3-diphenyl-acrylate (INCI octocrylene), 2-ethylhexyl-(2E)-3-(4-methoxyphenyl)acrylate (INCI ethylhexyl methoxy cinnamate) and benzylidene malonates according to the following preferred structures:

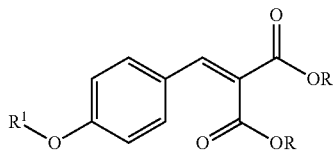

wherein
$R^1$ is methyl, ethyl, propyl or n-butyl;
if $R^1$ is methyl, then
R is tert. butyl or a radical of formula

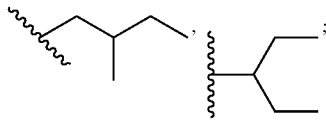

or a radical of formula

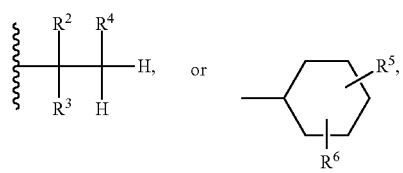

wherein
$R^2$ and $R^3$ are independently from each other hydrogen or methyl;
$R^4$ is methyl, ethyl or n-propyl;
$R^5$ and $R^6$ are independently from each other hydrogen or $C_1$-$C_3$-alkyl;

if $R^1$ is ethyl, propyl or n-butyl, then
R is isopropyl;
and wherein the composition comprises (i) to (ii) in a ratio of larger or equal to 0.8.

In a preferred embodiment of said composition, the sunscreen or daily care composition comprises (i) hexyl 2-[4-(diethylamino)-2-hydroxybenzoyl]benzoate (INCI diethylamino hydroxybenzoyl hexyl benzoate) and (ii) 1-(4-(1,1-dimethylethyl)phenyl)-3-(4-methoxyphenyl)propane-1,3-dione (INCI butyl methoxydibenzoylmethane) in a ratio of larger or equal to 1.

In a more preferred embodiment of said composition, the sunscreen or daily care composition comprises (i) hexyl 2-[4-(diethylamino)-2-hydroxybenzoyl]benzoate (INCI diethylamino hydroxybenzoyl hexyl benzoate) and (ii) 1-(4-(1,1-dimethylethyl)phenyl)-3-(4-methoxyphenyl)propane-1,3-dione (INCI butyl methoxydibenzoylmethane) in a ratio of from 1:1 to 10:1, preferably in a ratio of from 1:1 to 5:1, more preferably in a ratio of from 1:1 to 2:1 and even more preferably in a ratio of from 1:1 to 1.5:1.

In another preferred embodiment of said composition, the sunscreen or daily care composition is free of titanium dioxide and zinc oxide.

In another preferred embodiment of said composition, the sunscreen or daily care composition does not comprise 2-hydroxy-4-methoxybenzophenone (INCI oxybenzone) and isoamyl-4-methoxycinnamate (INCI isoamyl-p-methoxy cinnamate).

In another preferred embodiment of said composition, the sunscreen or daily care composition is free of parabens.

In another preferred embodiment of said composition, the sunscreen or daily care composition is provided in the form of a sprayable product.

In another preferred embodiment of said composition, the sunscreen or daily care composition is free of emulsifier.

In another preferred embodiment of said composition, the sunscreen or daily care composition is free of phenoxyethanol.

In another preferred embodiment of said composition, in the sunscreen or daily care composition the (iii) is an oil soluble UV filter or (iii) is 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) dissolved in a polymer matrix to be dispersible in water.

In another preferred embodiment of said composition, the sunscreen or daily care composition comprises hexyl 2-[4-(diethylamino)-2-hydroxybenzoyl]benzoate (INCI diethylamino hydroxybenzoyl hexyl benzoate) in an amount of from 1% to 10% by weight, based on the total weight of the composition.

In another preferred embodiment of said composition, the sunscreen or daily care composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

In another preferred embodiment of said composition, the sunscreen or daily care composition comprises 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) in an amount of from 0.5% to 5% by weight, preferably in an amount of from 0.8% to 3% by weight, based on the total weight of the composition.

In another preferred embodiment of said composition, the sunscreen or daily care composition comprises 4,4',4''-(1,3,5-triazine-2,4,6-triyltriimino)tris-benzoic acid-tris(2-ethylhexyl)ester (INCI ethylhexyl triazone) in an amount of from 0.5% to 5% by weight, preferably in an amount of from 0.8% to 3% by weight, based on the total weight of the composition.

In another preferred embodiment of said composition, the sunscreen or daily care composition comprises 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl) ester (INCI diethylhexyl-butamidotriazone) in an amount of from 0.5% to 5% by weight, preferably in an amount of from 0.8% to 3% by weight, based on the total weight of the composition.

In another preferred embodiment of said composition, the at least one organic particulate UV filter is selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 1,1'-(1,4-piperazinediyl)bis[1-[2-[4-(diethylamino)-2-hydroxy-benzoyl]phenyl]-methanone (INCI bis-(diethylaminohydroxybenzoyl benzoyl) piperazine), 5,6,5',6'-tetraphenyl-3-3'-(1,4-phenylene)bis(1,2,4-triazine) (INCI phenylene bis-diphenyltriazine), micronized 1,4-di(benzoxazole-2'-yl)benzene and combinations thereof.

In another preferred embodiment of said composition, the sunscreen or daily care composition has a sun protection factor (SPF) of at least 20.

In another preferred embodiment of said composition, the sunscreen or daily care composition has a b* value of <25.

In another aspect the present invention relates to the use of a sunscreen or daily care composition to reduce sand adhesion on the skin, wherein the composition comprises (i) hexyl 2-[4-(diethylamino)-2-hydroxybenzoyl]benzoate (INCI diethylamino hydroxybenzoyl hexyl benzoate); and (ii) 1-(4-(1,1-dimethylethyl)phenyl)-3-(4-methoxyphenyl)propane-1,3-dione (INCI butyl methoxydibenzoylmethane); and (iii) 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine); and (iv) 4,4',4"-(1,3,5-triazine-2,4,6-triyltriimino)tris-benzoic acid-tris(2-ethylhexyl)ester (INCI ethylhexyl triazone) and/or 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone); and (v) at least one organic particulate UV filter, wherein the composition is free of ethylhexyl-2-cyano-3,3-diphenyl-acrylate (INCI octocrylene), 2-ethylhexyl-(2E)-3-(4-methoxyphenyl)acrylate (INCI ethylhexyl methoxy cinnamate) and benzylidene malonates according to the following preferred structures:

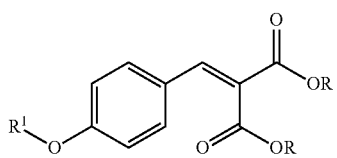

wherein
$R^1$ is methyl, ethyl, propyl or n-butyl;
if $R^1$ is methyl, then
R is tert. butyl or a radical of formula

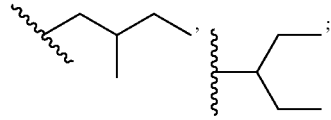

or a radical of formula

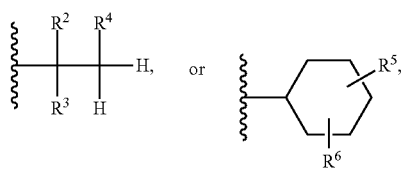

wherein
$R^2$ and $R^3$ are independently from each other hydrogen or methyl;
$R^4$ is methyl, ethyl or n-propyl;
$R^5$ and $R^6$ are independently from each other hydrogen or $C_1$-$C_3$-alkyl;
if $R^1$ is ethyl, propyl or n-butyl, then
R is isopropyl;
and wherein the composition comprises (i) to (ii) in a ratio of larger or equal to 0.8.

In a preferred embodiment of said use, the sunscreen or daily care composition comprises (i) hexyl 2-[4-(diethylamino)-2-hydroxybenzoyl]benzoate (INCI diethylamino hydroxybenzoyl hexyl benzoate) and (ii) 1-(4-(1,1-dimethylethyl)phenyl)-3-(4-methoxyphenyl)propane-1,3-dione (INCI butyl methoxydibenzoylmethane) in a ratio of larger or equal to 1.

In a more preferred embodiment of said use, the sunscreen or daily care composition comprises (i) hexyl 2-[4-(diethylamino)-2-hydroxybenzoyl]benzoate (INCI diethylamino hydroxybenzoyl hexyl benzoate) and (ii) 1-(4-(1,1-dimethylethyl)phenyl)-3-(4-methoxyphenyl)propane-1,3-dione (INCI butyl methoxydibenzoylmethane) in a ratio of from 1:1 to 10:1, preferably in a ratio of from 1:1 to 5:1, more preferably in a ratio of from 1:1 to 2:1 and even more preferably in a ratio of from 1:1 to 1.5:1.

In another preferred embodiment of said use, the sunscreen or daily care composition is free of titanium dioxide and zinc oxide.

In another preferred embodiment of said use, the sunscreen or daily care composition does not comprise 2-hydroxy-4-methoxybenzophenone (INCI oxybenzone) and isoamyl-4-methoxycinnamate (INCI isoamyl-p-methoxy cinnamate).

In another preferred embodiment of said use, the sunscreen or daily care composition is free of parabens.

In another preferred embodiment of said use, the sunscreen or daily care composition is provided in the form of a sprayable product.

In another preferred embodiment of said use, the sunscreen or daily care composition is free of emulsifier.

In another preferred embodiment of said use, the sunscreen or daily care composition is free of phenoxyethanol.

In another preferred embodiment of said use, in the sunscreen or daily care composition the (iii) is an oil soluble UV filter or (iii) is 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) dissolved in a polymer matrix to be dispersible in water.

In another preferred embodiment of said use, the sunscreen or daily care composition comprises hexyl 2-[4-(diethylamino)-2-hydroxybenzoyl]benzoate (INCI diethylamino hydroxybenzoyl hexyl benzoate) in an amount of from 1% to 10% by weight, based on the total weight of the composition.

In another preferred embodiment of said use, the sunscreen or daily care composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

In another preferred embodiment of said use, the sunscreen or daily care composition comprises 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) in an amount of from 0.5% to 5% by weight, preferably in an amount of from 0.8% to 3% by weight, based on the total weight of the composition.

In another preferred embodiment of said use, the sunscreen or daily care composition comprises 4,4',4"-(1,3,5-triazine-2,4,6-triyltriimino)tris-benzoic acid-tris(2-ethylhexyl)ester (INCI ethylhexyl triazone) in an amount of from 0.5% to 5% by weight, preferably in an amount of from 0.8% to 3% by weight, based on the total weight of the composition.

In another preferred embodiment of said use, the sunscreen or daily care composition comprises 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone) in an amount of from 0.5% to 5% by weight, preferably in an amount of from 0.8% to 3% by weight, based on the total weight of the composition.

In another preferred embodiment of said use, the at least one organic particulate UV filter is selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 1,1'-(1,4-piperazinediyl)bis[1-[2-[4-(diethylamino)-2-hydroxybenzoyl]phenyl]-methanone (INCI bis-(diethylaminohydroxybenzoyl benzoyl) piperazine), 5,6,5',6'-tetraphenyl-3-3'-(1,4-phenylene)bis(1,2,4-triazine) (INCI phenylene bis-diphenyltriazine), micronized 1,4-di(benzoxazole-2'-yl)benzene and combinations thereof.

In another preferred embodiment of said use, the sunscreen or daily care composition has a sun protection factor (SPF) of at least 20.

In another preferred embodiment of said use, the sunscreen or daily care composition has a b* value of <25.

In another aspect the present invention relates to the use of a sunscreen or daily care composition for the administration to sensitive skin, wherein the composition comprises
(i) hexyl 2-[4-(diethylamino)-2-hydroxybenzoyl]benzoate (INCI diethylamino hydroxybenzoyl hexyl benzoate); and
(ii) 1-(4-(1,1-dimethylethyl)phenyl)-3-(4-methoxyphenyl)propane-1,3-dione (INCI butyl methoxydibenzoylmethane); and
(iii) 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine); and
(iv) 4,4',4"-(1,3,5-triazine-2,4,6-triyltriimino)tris-benzoic acid-tris(2-ethylhexyl)ester (INCI ethylhexyl triazone) and/or 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone),
wherein the composition is free of ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate); and wherein the composition comprises (i) to (ii) in a ratio of larger or equal to 0.8.

In a preferred embodiment of said use, the sunscreen or daily care composition comprises (i) hexyl 2-[4-(diethylamino)-2-hydroxybenzoyl]benzoate (INCI diethylamino hydroxybenzoyl hexyl benzoate) and (ii) 1-(4-(1,1-dimethylethyl)phenyl)-3-(4-methoxyphenyl)propane-1,3-dione (INCI butyl methoxydibenzoylmethane) in a ratio of larger or equal to 1.

In a more preferred embodiment of said use, the sunscreen or daily care composition comprises (i) hexyl 2-[4-(diethylamino)-2-hydroxybenzoyl]benzoate (INCI diethylamino hydroxybenzoyl hexyl benzoate) and (ii) 1-(4-(1,1-dimethylethyl)phenyl)-3-(4-methoxyphenyl)propane-1,3-dione (INCI butyl methoxydibenzoylmethane) in a ratio of from 1:1 to 10:1, preferably in a ratio of from 1:1 to 5:1, more preferably in a ratio of from 1:1 to 2:1 and even more preferably in a ratio of from 1:1 to 1.5:1.

In another preferred embodiment of said use, the sunscreen or daily care composition is free of titanium dioxide, and zinc oxide.

In another preferred embodiment of said use, the sunscreen or daily care composition does not comprise 2-hydroxy-4-methoxybenzophenone (INCI oxybenzone) and isoamyl-4-methoxycinnamate (INCI isoamyl-p-methoxy cinnamate).

In another preferred embodiment of said use, the sunscreen or daily care composition is free of parabens.

In another preferred embodiment of said use, the sunscreen or daily care composition is provided in the form of a sprayable product.

In another preferred embodiment of said use, the sunscreen or daily care composition is free of emulsifier.

In another preferred embodiment of said use, the sunscreen or daily care composition is free of phenoxyethanol.

In another preferred embodiment of said use, in the sunscreen or daily care composition the (iii) is an oil soluble UV filter or (iii) is 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) dissolved in a polymer matrix to be dispersible in water.

In another preferred embodiment of said use, the sunscreen or daily care composition comprises hexyl 2-[4-(diethylamino)-2-hydroxybenzoyl]benzoate (INCI diethylamino hydroxybenzoyl hexyl benzoate) in an amount of from 1% to 10% by weight, based on the total weight of the composition.

In another preferred embodiment of said use, the sunscreen or daily care composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

In another preferred embodiment of said use, the sunscreen or daily care composition comprises 2,4-bis-{[4-(2- ethyl-hexyloxy)-2-hydroxy]-phenyl}-6-(4-methoxyphenyl)-1,3,5 triazine (INCI bis-ethylhexyloxyphenol methoxyphenyl triazine) in an amount of from 0.5% to 5% by weight, preferably in an amount of from 0.8% to 3% by weight, based on the total weight of the composition.

In another preferred embodiment of said use, the sunscreen or daily care composition comprises 4,4',4"-(1,3,5-triazine-2,4,6-triyltriimino)tris-benzoic acid-tris(2-ethylhexyl)ester (INCI ethylhexyl triazone) in an amount of from 0.5% to 5% by weight, preferably in an amount of from 0.8% to 3% by weight, based on the total weight of the composition.

In another preferred embodiment of said use, the sunscreen or daily care composition comprises 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl) ester (INCI diethylhexyl-butamidotriazone) in an amount of from 0.5% to 5% by weight, preferably in an amount of from 0.8% to 3% by weight, based on the total weight of the composition.

In another preferred embodiment of said use, the sunscreen or daily care composition has a sun protection factor (SPF) of at least 20.

Before describing preferred embodiments of the present invention in detail, definitions important for understanding the present invention are given.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention, the term "consisting of" is considered to be a preferred embodiment of the term "comprising of". If hereinafter a group is defined to comprise at least a certain number of embodiments, this is meant to also encompass a group, which preferably consists of these embodiments only.

Furthermore, the terms "first", "second", "third" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

As used herein the term "free of" means in the context that the composition of the present invention is free of a specific compound or group of compounds, which may be combined under a collective term, that the composition does not comprise said compound or group of compounds in an amount of more than 0.8% by weight, based on the total weight of the composition. In other words, the composition is substantially free of a specific compound or group of compounds. Furthermore, it is preferred that the composition according to the present invention does not comprise said compounds or group of compounds in an amount of more than 0.5% by weight, preferably the composition does not comprise said compounds or group of compounds at all. The same definition is applied for the term "does not comprise".

Furthermore, it is to be understood that the term 'free of' or "does not comprise", in case the composition does not comprise a compound X and a compound Y means that the compositions must be free of both compounds X and Y. In other words, the composition may not contain any compound selected from X and Y.

The term "sunscreen composition" refers to any topical product, which reflects and/or absorbs certain parts of UV radiation. Thus, the term "sunscreen composition" is to be understood as not only including sunscreen compositions, but also any cosmetic compositions that provide UV protection. The term "topical product" refers to a product that is applied to the skin and can refer, e.g., to sprays, lotions, creams, oils, or gels. The sunscreen composition may comprise one or more active agents, e.g., organic or inorganic UV filters, as well as other ingredients or additives, e.g., emulsifiers, emollients, viscosity regulators, stabilizers, preservatives, or fragrances.

The term "daily care composition" refers to any topical product, which reflects and/or absorbs certain parts of UV radiation and is used as an everyday care product for the human body, e.g., for face, body or hair. The daily care composition may comprise one or more active agents, e.g., organic or inorganic UV filters, as well as other ingredients or additives, e.g., emulsifiers, emollients, viscosity regulators, stabilizers, preservatives, or fragrances.

The term "UV-filter" as used herein refers to organic or inorganic compounds, which can absorb and/or reflect UV radiation caused by sunlight. UV-filter can be classified based on their UV protection curve as UV-A, UV-B or broadband filters. In the context of the present application, broadband filters may be listed as UV-A filters, as they also provide UV-A protection. In other words, preferred UV-A filters also include broadband filters.

Water soluble UV filters have a solubility in water of at least 2% by weight, preferably at least 3% by weight, more preferably at least 5% by weight.

Oil soluble UV filters have a solubility in common cosmetic oils, such as $C_{12}$-$C_{15}$-alkyl benzoate, dibutyl adipate, diisopropyl sebacate, phenethyl benzoate, or dicaprylyl carbonate of at least 2% by weight, preferably at least 5% by weight, more preferably at least 7% by weight.

Particulate UV filters can be further divided into organic particulate UV filters and inorganic particulate UV filters. While organic particulate UV filters are based on organic compounds, inorganic particulate UV filters are based on inorganic compounds such as titanium dioxide and zinc oxide. Particulate UV filters have a solubility of less than 0.01% by weight, preferably less than 0.05% by weight in the sunscreen composition, i.e. in the water and the cosmetic oils contained therein. Preferably, the particulate UV filters have a particle size $D_N50$ determined by light scattering of less than 2000 nm, preferably less than 1000 nm, wherein $D_N50$ refers to the particle size value, where half of the population lies below this value, and half of the population lies above this value, i.e. the median value of the particle size volume distribution.

Nano-particulate UV filters preferably exhibit a $D_N$ 50 higher than 60 nm and a $D_N90$ higher than 90 nm.

Hexyl 2-[4-(diethylamino)-2-hydroxybenzoyl]benzoate (INCI diethylamino hydroxybenzoyl hexyl benzoate) is an oil soluble UV-A filter, which has an absorption maximum at 354 nm. Diethylamino hydroxybenzoyl hexyl benzoate has an excellent photo stability for long-lasting protection of the skin and provides an efficient shielding against UV-A I and UV-A II radiation. It is sold under the trade name Uvinul® A Plus by BASF.

1-(4-(1,1-dimethylethyl)phenyl)-3-(4-methoxyphenyl) propane-1,3-dione (INCI butyl methoxydibenzoylmethane) is a soluble organic UV-A filter. It absorbs UV-A radiation in the range of from 320 nm to 400 nm with an absorption maximum at 357 nm.

2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) is one of the most efficient oil soluble broad band UV filter with an excellent photo stability to provide a long lasting protection of the skin. It is sold by BASF under the trade name Tinosorb® S. Tinosorb S has a high contribution to the sun protection factor and the UV-A protection factor already at low concentrations. Tinosorb® S can be either an oil soluble UV filter or it can be applied in the water phase when dissolved in a polyacrylate matrix. With regard to the latter, it is sold under the trade name Tinosorb® S Aqua or Tinosorb S Lite Aqua by BASF.

4,4',4"-(1,3,5-triazine-2,4,6-triyltriimino)tris-benzoic acid-tris(2-ethylhexyl)ester (INCI ethylhexyl triazone) is an UV-B absorber with a high efficiency also at low concentrations. It is a highly stable UV-B filter. Ethylhexyl triazone is sold under the trade name Uvinul® T 150 by BASF.

4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone) is a soluble organic UV-B filter which absorbs in the range of from 280 nm to 320 nm. It has an absorption maximum at 310 nm. Diethylhexyl butamidotriazone is sold by 3V Sigma under the trade name Uvasorb HEB.

Ethylhexyl-2-cyano-3,3-diphenyl-acrylate (INCI octocrylene) is an oil soluble organic UV-B filter with an absorption maximum at 302 nm. It provides a broad UV-B absorbance and is known to be an efficient stabilizer for photounstable UV filters. Octocrylene is sold by BASF under the tradename Uvinul® N 539 T.

2-Ethylhexyl-(2E)-3-(4-methoxyphenyl)acrylate (INCI ethylhexyl methoxy cinnamate) is an odorless and colorless UV-B filter with an absorption maximum at 310 nm. It is a good solvent for other crystalline UV filters. Ethylhexyl methoxy cinnamate is sold under the tradename Uvinul® MC 80 by BASF.

The term "alkyl" as used herein denotes in each case a straight-chain or branched alkyl group having usually from 1 to 10 carbon atoms, preferably from 1 to 6 carbon atoms, even more preferably from 1 to 4 carbon atoms. Exemplified alkyl groups include methyl, ethyl, n-propyl, iso-propyl, n-butyl, 2-butyl, iso-butyl, tert.-butyl, n-pentyl, 1-methylbutyl, 2-methylbutyl, 3-methylbutyl, and 2,2-dimethylpropyl. Methyl, ethyl, n-propyl and iso-propyl are particularly preferred.

The term "paraben" refers to a class of preservatives used in cosmetic and pharmaceutical compositions. They are commonly used due to their bactericidal and fungicidal properties. The chemical structure of parabens is based on parahydroxybenzoates or esters of parahydroxybenzoic acid, e.g. methylparaben, ethylparaben, propylparaben, butylparaben or heptylparaben.

The term "emollient" relates to cosmetic preparations used for protecting, moisturizing and lubricating the skin. The word emollient is derived from the Latin word mollire, to soften. In general, emollients prevent evaporation of water from the skin by forming an occlusive coating. They can be divided into different groups depending on their polarity index.

The term "polarity index" refers to non-polar or polar oils. Non-polar oils are mainly based on hydrocarbons and lack an electronegative element, such as oxygen. In contrast, polar oils contain heteroatoms that differ in electronegativity, which results in a dipole moment. However, such oils are still insoluble in water, i.e. hydrophob. The polarity index can be determined by measuring the interfacial tension between the respective oil and water.

The term "$C_{12}$-$C_{15}$ alkyl benzoate" refers to esters of benzoic acid with fatty alcohols containing a $C_{12}$-$C_{15}$-alkyl chain. $C_{12}$-$C_{15}$ alkyl chain is defined as an alkyl chain with $C_{12}$, $C_{13}$, $C_{14}$ or $C_{15}$ chain length.

The term "dispersible in" as used herein indicates that a certain compound is not soluble in the respective water or oil phase, but finely dispersed in the respective phase.

The term "polymer matrix" as used herein is directed to matrices, which consist of multiple polymer chains grouped in a way to entrap, enclose or also dissolve particles, such as different organic compounds.

The term "sensitive skin" refers to skin of which the natural barrier function is weakened and has broken due to a trigger. A trigger can be for example cold weather, extremely hot water, emulsifier or preservatives, which are often included in sunscreen or daily care compositions.

The term "sun protection factor (SPF)" as used herein indicates how well the skin is protected by a sunscreen composition mainly from UV-B radiation. In particular, the factor indicates how much longer the protected skin may be exposed to the sun without getting a sunburn in comparison to untreated skin. For example, if a sunscreen composition with an SPF of 15 is evenly applied to the skin of a person usually getting a sunburn after 10 minutes in the sun, the sunscreen allows the skilled person to stay in the sun 15 times longer. In other words, SPF 15 means that $\frac{1}{15}$ of the burning UV radiation will reach the skin, assuming sunscreen is applied evenly at a thick dosage of 2 milligrams per square centimeter ($mg/cm^2$).

The definition of "broadband" protection (also referred to as broad-spectrum or broad protection) is based on the "critical wavelength". For broadband coverage, UV-B and UV-A protection must be provided. According to the US requirements, a critical wavelength of at least 370 nm is required for achieving broad spectrum protection. Furthermore, it is recommended by the European Commission that all sunscreen or cosmetic compositions should have an UVA protection factor, which is at least one third of the labelled sun protection factor (SPF), e.g. if the sunscreen composition has an SPF of 30 the UVA protection factor has to be at least 10.

The term "administration" refers to the application of a sunscreen or daily care composition to the skin of a person.

Preferred embodiments regarding the sunscreen or daily care composition according to the present application as well as the use of said composition are described hereinafter. It is to be understood that the preferred embodiments of the invention are preferred alone or in combination with each other.

As indicated above, the present invention relates in one embodiment to a sunscreen or daily care composition comprising
(i) hexyl 2-[4-(diethylamino)-2-hydroxybenzoyl]benzoate (INCI diethylamino hydroxybenzoyl hexyl benzoate); and
(ii) 1-(4-(1,1-dimethylethyl)phenyl)-3-(4-methoxyphenyl)propane-1,3-dione (INCI butyl methoxydibenzoylmethane); and
(iii) 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine); and (iv) optionally comprising 4,4',4''-(1,3,5-triazine-2,4,6-triyltriimino)tris-benzoic acid-tris(2-ethylhexyl)ester (INCI ethylhexyl triazone) and/or 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone), wherein the composition is free of ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate); and wherein the composition comprises (i) to (ii) in a ratio of larger or equal to 0.8.

In connection with the present invention, the following preferred embodiments regarding the sunscreen composition are relevant.

In a first embodiment of the present invention, the sunscreen or daily care composition comprises
diethylamino hydroxybenzoyl hexyl benzoate,
butyl methoxydibenzoylmethane,
bis-ethylhexyloxyphenol methoxyphenyl triazine, and
ethylhexyl triazone,
wherein the composition is free of ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate).

In a second embodiment of the present invention, the sunscreen or daily care composition comprises
diethylamino hydroxybenzoyl hexyl benzoate,
butyl methoxydibenzoylmethane,
bis-ethylhexyloxyphenol methoxyphenyl triazine, and
diethylhexyl-butamidotriazone,
wherein the composition is free of ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate).

In a third embodiment of the present invention, the sunscreen or daily care composition comprises
diethylamino hydroxybenzoyl hexyl benzoate,
butyl methoxydibenzoylmethane,
bis-ethylhexyloxyphenol methoxyphenyl triazine,
ethylhexyl triazone, and
diethylhexyl-butamidotriazone,
wherein the composition is free of ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate).

In a particularly preferred embodiment of the present invention, the sunscreen or daily care composition as defined above with regard to the first, second and third embodiment, comprises at least one additional UV filter, wherein the at least one additional UV filter is at least one organic particulate UV filter.

Thus, in a particularly preferred embodiment of the present invention, the sunscreen or daily care composition comprises
(i) hexyl 2-[4-(diethylamino)-2-hydroxybenzoyl]benzoate (INCI diethylamino hydroxybenzoyl hexyl benzoate); and
(ii) 1-(4-(1,1-dimethylethyl)phenyl)-3-(4-methoxyphenyl)propane-1,3-dione (INCI butyl methoxydibenzoylmethane); and
(iii) 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine); and
(iv) 4,4',4''-(1,3,5-triazine-2,4,6-triyltriimino)tris-benzoic acid-tris(2-ethylhexyl)ester (INCI ethylhexyl triazone) and/or 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone); and
(v) at least one organic particulate UV filter,
wherein the composition is free of ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate).

In connection with the above embodiments, it is to be understood that the composition is further free of benzylidene malonates according to the following preferred structures:

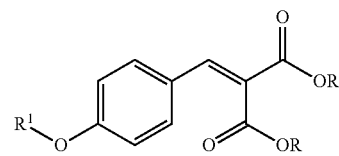

wherein
$R^1$ is methyl, ethyl, propyl or n-butyl;
if $R^1$ is methyl, then
R is tert. butyl or a radical of formula

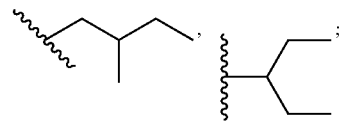

or a radical of formula

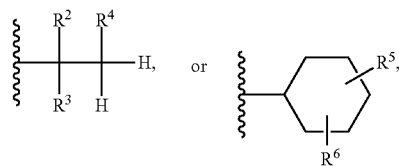

wherein
$R^2$ and $R^3$ are independently from each other hydrogen or methyl;
$R^4$ is methyl, ethyl or n-propyl;
$R^5$ and $R^6$ are independently from each other hydrogen or $C_1$-$C_3$-alkyl;
if $R^1$ is ethyl, propyl or n-butyl, then
R is isopropyl.

Thus, in a particularly preferred embodiment of the present invention, the sunscreen or daily care composition comprises
(i) hexyl 2-[4-(diethylamino)-2-hydroxybenzoyl]benzoate (INCI diethylamino hydroxybenzoyl hexyl benzoate); and
(ii) 1-(4-(1,1-dimethylethyl)phenyl)-3-(4-methoxyphenyl)propane-1,3-dione (INCI butyl methoxydibenzoylmethane); and
(iii) 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine); and
(iv) 4,4',4''-(1,3,5-triazine-2,4,6-triyltriimino)tris-benzoic acid-tris(2-ethylhexyl)ester (INCI ethylhexyl triazone) and/or 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethyl-hexyl-butamidotriazone); and (v) at least one organic particulate UV filter, wherein the composition is free of ethylhexyl-2-cyano-3,3-diphenyl-acrylate (INCI octocrylene), 2-ethylhexyl-(2E)-3-(4-methoxyphenyl)acrylate (INCI ethylhexyl methoxy cinnamate) and benzylidene malonates according to the following preferred structures:

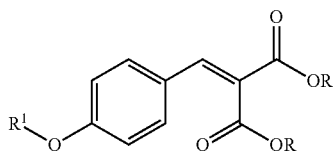

wherein
$R^1$ is methyl, ethyl, propyl or n-butyl;
if $R^1$ is methyl, then
R is tert. butyl or a radical of formula

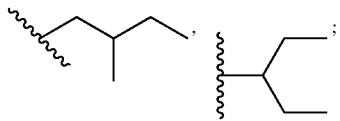

or a radical of formula

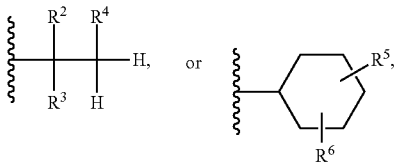

wherein
$R^2$ and $R^3$ are independently from each other hydrogen or methyl;
$R^4$ is methyl, ethyl or n-propyl;
$R^5$ and $R^6$ are independently from each other hydrogen or $C_1$-$C_3$-alkyl;
if $R^1$ is ethyl, propyl or n-butyl, then
R is isopropyl.

In another preferred embodiment of the present invention, the sunscreen or daily care composition as defined above does not comprise benzylidene malonates.

In connection with the above embodiments, in particular in connection with the first, second and third embodiment, it is further preferred that the sunscreen or daily care composition comprises hexyl 2-[4-(diethylamino)-2-hydroxybenzoyl]benzoate (INCI diethylamino hydroxybenzoyl hexyl benzoate) and 1-(4-(1,1-dimethylethyl)phenyl)-3-(4-methoxyphenyl)propane-1,3-dione (INCI butyl methoxydibenzoylmethane) in a ratio of larger or equal to 0.8.

In this connection, it is to be understood that a ratio of larger or equal to 0.8 means that hexyl 2-[4-(diethylamino)-2-hydroxybenzoyl]benzoate (INCI diethylamino hydroxybenzoyl hexyl benzoate) and 1-(4-(1,1-dimethylethyl)phenyl)-3-(4-methoxyphenyl)propane-1,3-dione (INCI butyl methoxydibenzoylmethane) are either present in a ratio of 1:1.2, or that hexyl 2-[4-(diethylamino)-2-hydroxybenzoyl]benzoate (INCI diethylamino hydroxybenzoyl hexyl benzoate) and 1-(4-(1,1-dimethylethyl)phenyl)-3-(4-methoxyphenyl)propane-1,3-dione (INCI butyl methoxydibenzoylmethane) are present in a ratio of larger than 1:1.2. In other words, a ratio of larger than 0.8 or 1:1.2 preferably means that diethylamino hydroxybenzoyl hexyl benzoate is present in the sunscreen or daily care composition in the same amount as butyl methoxydibenzoylmethane or in a higher amount as butyl methoxydibenzoylmethane, e.g. in a ratio of from 1:1 to 10:1.

Further, in connection with the above embodiments it is to be understood that free of means that the composition does not comprise octocrylene and ethylhexyl methoxy cinnamate. In particular, it is to be understood that the composition does not comprise octocrylene and ethylhexyl methoxy cinnamate in an overall amount of more than 0.8% by weight, based on the total weight of the composition. Furthermore, it is to be understood that the composition does not comprise octocrylene and ethylhexyl methoxy cinnamate in an overall amount of more than 0.5% by weight.

In a preferred embodiment of the present invention, the sunscreen or daily care composition as defined above does not comprise octocrylene and ethylhexyl methoxy cinnamate at all.

In another preferred embodiment of the present invention, the sunscreen or daily care composition as defined above comprises at least one organic particulate UV filter, wherein the at least one organic particulate UV filter is selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris (biphenyl-4-yl)-1,3,5-triazine (INCI trisbiphenyl triazine), 1,1'-(1,4-piperazinediyl)bis[1-[2-[4-(diethylamino)-2-hydroxybenzoyl]phenyl]-methanone (INCI bis-(diethylaminohydroxybenzoyl benzoyl) piperazine), 5,6,5',6'-tetraphenyl-3-3'-(1,4-phenylene)bis(1,2,4-triazine) (INCI phenylene bis-diphenyltriazine), micronized 1,4-di(benzoxazole-2'-yl) benzene and combinations thereof.

In one embodiment of the present invention, the sunscreen or daily care composition as defined above further comprises at least one emollient with a polarity index of <30 mN/m.

In a preferred embodiment of the present invention, the sunscreen or daily care composition as defined above further comprises at least one emollient with a polarity index of <30 mN/m selected from
  esters of linear or branched fatty acids with linear or branched fatty alcohols;
  esters of aromatic carboxylic acids with linear or branched fatty alcohols;
  di- and tricarboxylic acid esters with linear or branched alcohols;
  esters of hydroxycarboxylic acids with linear or branched fatty alcohols;
  esters of linear or branched fatty acids with polyhydric alcohol;
  mono-, di-, tri-glycerides based on $C_6$-$C_{18}$ fatty acids;
  Guerbet alcohols.

In a more preferred embodiment of the present invention, the sunscreen or daily care composition as defined above further comprises at least one emollient with a polarity index of <30 mN/m selected from the group consisting of $C_{12}$-$C_{15}$ alkyl benzoate, caprylic/capric triglyceride, butylene glycol dicaprylate/dicaprate, propylene glycol dicaprylate/dicaprate, diisopropyl sebacate, octyldodecanol, isopropyl palmitate, isopropyl myristate, dicaprylyl carbonate, phenethyl benzoate, dibutyl adipate, diisopropyl adipate, triethyl citrate and tributyl citrate.

In a preferred embodiment, the sunscreen or daily care composition comprises the at least one emollient in an amount of from 1% to 20% by weight, preferably in an amount of from 2% to 15% by weight, based on the total weight of the sunscreen or daily care composition. It is to be understood that these amounts refer to each individual emollient in the sunscreen or daily care composition. Thus, each individual emollient in the sunscreen or daily care composition is preferably present in an amount of from 1% to 20% by weight, preferably in an amount of from 2% to 15% by weight, based on the total weight of the sunscreen or daily care composition. If two or more emollients are present in the sunscreen or daily care composition, the overall amount of emollients may preferably be in the range of from 1% to 35% by weight, preferably from 2% to 25% by weight, based on the total weight of the sunscreen or daily care composition.

In connection with the above preferred embodiments regarding the addition of the at least one emollient with a polarity index of <30 mN/m, it has surprisingly been found by the inventors of the present invention that the addition of at least one emollient as defined above enhances the solubility properties and performance of the UV filters as defined above in an octocrylene free sunscreen or daily care composition. In this connection, it is to be understood that the wavelength of maximum absorbance (λmax) is an indicator to describe the performance of a UV filter molecule. It gives the wavelength at which the absorbance is at maximum.

The following preferences regarding the ratio of diethylamino hydroxybenzoyl hexyl benzoate and butyl methoxydibenzoylmethane are relevant in connection with the above listed embodiments of the invention.

In one preferred embodiment of the present invention, the sunscreen or daily care composition according to the first, second and third embodiment as defined above comprises diethylamino hydroxybenzoyl hexyl benzoate (DHHB) and butyl methoxydibenzoylmethane (BMDBM) in a ratio of larger or equal to 1.

In another preferred embodiment of the present invention, the sunscreen or daily care composition according to the first, second and third embodiment as defined above comprises diethylamino hydroxybenzoyl hexyl benzoate and butyl methoxydibenzoylmethane in a ratio of from 1:1 to 10:1. In this regard, it is more preferred that the composition according to the first, second and third embodiment as defined above comprises diethylamino hydroxybenzoyl hexyl benzoate and butyl methoxydibenzoylmethane in a ratio of from 1:1 to 5:1.

In yet another preferred embodiment of the present invention, the sunscreen or daily care composition according to the first, second and third embodiment as defined above comprises diethylamino hydroxybenzoyl hexyl benzoate and butyl methoxydibenzoylmethane in a ratio of from 1:1 to 2:1 and more preferred in a ratio of from 1:1 to 1.5:1.

In a particularly preferred embodiment of the present invention, the sunscreen or daily care composition according to the first, second and third embodiment as defined above comprises diethylamino hydroxybenzoyl hexyl benzoate and butyl methoxydibenzoylmethane in a ratio of 1:1, 1.5:1, 1.7:1, 2:1 or 2.5:1.

In connection with the above preferred embodiments it is to be understood that the ratios as defined above for diethylamino hydroxybenzoyl hexyl benzoate and butyl methoxydibenzoylmethane are applied independently of any UV filters, which are additionally present in the sunscreen or daily care composition.

In connection with the above preferred embodiments regarding the sunscreen composition, in particular with regard to the UV filter DHHB, BMDBM and BEMT, it has surprisingly been found by the inventors of the present invention that DHHB stabilizes the UV filter BMDBM and BEMT. A skilled person is aware, that BMDBM is a frequently used UV absorber, which tends to isomerize under radiation to build a diketone in the triplet state. This diketone is very likely to undergo photolysis leading to a degradation of BMDBM. Furthermore, it has been found that the presence of BMDBM destabilizes the UV filter BEMT. Therefore, stabilizing agents need to be added to compositions comprising BMDBM, for example photo stable UV absorber such as octocrylene are commonly used. Thus, it has been a surprising finding by the inventors of the present invention, that BMDBM and BEMT can be stabilized in an octocrylene free sunscreen composition by using the UV filter DHHB.

The following preferences regarding the absence of specific UV filters or additives in the sunscreen or daily care composition are relevant in connection with the above listed embodiments of the invention.

In one embodiment of the present invention, the sunscreen or daily care composition as defined above is free of titanium dioxide and zinc oxide In another embodiment of the present invention, the sunscreen or daily care composition as defined above does not comprise 2-hydroxy-4-methoxybenzophenone (INCI oxybenzone) and isoamyl-4-methoxycinnamate (INCI isoamyl-p-methoxy cinnamate).

In yet another embodiment of the present invention, the sunscreen or daily care composition as defined above is free of parabens. In this connection, it is to be understood that parabens are also known by the synonyms parahydroxybenzoate, oxybenzoates, oxybenzoic acid, hydroxybenzoic acid, and hydroxybenzoate, which are also excluded from the sunscreen or daily care composition according to the present invention.

Possible parabens, which are excluded from the sunscreen or daily care composition according to the present invention, are butyl paraben, ethyl paraben or methyl paraben, propyl paraben, isobutyl paraben, isopropyl paraben, sodium paraben, sodium methyl paraben, sodium propyl paraben, potassium paraben and calcium paraben.

In yet another embodiment of the present invention, the sunscreen or daily care composition according to the present invention is free of phosphate-based emulsifier, such as potassium cetyl phosphate and $C_{20-22}$-alkyl phosphate.

In yet another embodiment of the present invention, the sunscreen or daily care composition is free of any emulsifier. In this connection it is to be understood that the term "emulsifiers", which are also known as emulgents, typically refers to compounds, which stabilize an emulsion by increasing its kinetic stability. In principle, they consist of a polar or hydrophilic part and a non-polar or hydrophobic part.

Possible emulsifiers, which are excluded from the sunscreen or daily care composition according to the present invention, are for example selected from the group consisting of glucose derivatives such as cetearyl glucoside, arachidyl glucoside, lauryl glucoside, polyglyceryl-3 methylglucose distearate, methyl glucose sesquistearate;

sucrose derivative such as sucrose polystearate, sucrose palmitate;
sorbitol derivatives such as polysorbate-n, PEG-10 sorbitan laurate;
fatty alcohol polyglycolethers and fatty acid polyglycolethers such as ceteareth-20, beheneth-25, steareth-2, PEG-100 stearate;
glycerides of fatty acids such as glyceryl stearate, glyceryl oleate;
glumatic acid derivatives such as sodium stearoyl glutamate;
sulfosuccinic acid derivatives such as disodium cetearyl sulfosuccinate;
phosphoric acid derivatives such as potassium cetyl phosphate;
fatty acid esters of polyglyceryl such as polyglyceryl-3-diisostearate, polyglyceryl-2-dipolyhydroxystearate;
oxyalkenylated organomodified silicone/polysiloxane/polyalkyl/polyether copolymers and derivatives.

In connection with the above embodiment, it is to be understood that the sunscreen or daily care composition may optionally comprise polymers instead of emulsifiers, which act in the same manner as an emulsifier. The sunscreen or daily care composition according to the present invention may include a polymer selected from the group consisting of
acrylates/C10-30 alkyl acrylate crosspolymer;
ammonium acryloyldimethyltaurateNP copolymer;
sodium acryloyldimethyltaurateNP crosspolymer;
sodium polyacryloyldimethyltaurate;
acrylates/behenteh-25 methacrylate copolymer;
sodium polyacrylate;
polyacrylate 13;
polyacrylate crosspolymer-11;
polyacrylate crosspolymer-6;
acrylates/vinyl isodecanoate crosspolymer;
carbomer
polyacrylamide; and
ammonium acryloyldimethyltaurate/carboxyethyl acrylate crosspolymer.

As indicated above, the sunscreen or daily care composition may further comprise polymers. In this regard, it is to be understood that the composition may optionally comprise one or more polymers selected from the group as defined above.

In a preferred embodiment of the present invention, the sunscreen or daily care composition comprises at least one polymer selected from the group as defined above. In a more preferred embodiment of the present invention, the composition comprises two or more polymers selected from the group as defined above. In this connection, it is to be understood that preferred polymers are selected from the group consisting of acrylates/C10-30 alkyl acrylate crosspolymer, acrylates/behenteh-25 methacrylate copolymer, carbomer and sodium polyacrylate.

In yet another embodiment of the present invention, the sunscreen or daily care composition is free of phenoxyethanol.

In yet another embodiment of the present invention, the sunscreen or daily care composition as defined above is free of (RS)-2-ethylhexyl-2-hydroxybenzoate (INCI ethylhexyl salicylate) and 3,3,5-trimethyl-cyclohexyl salicylate (homosalate).

In connection with the above embodiments, it is to be understood, that the sunscreen or daily care composition as defined above according to the present invention is free of the substances as defined above alone or further does not comprise the combinations as outlined below.

Thus, in one preferred embodiment of the present invention, the sunscreen or daily care composition as defined above further is free of
titanium dioxide and zinc oxide;
oxybenzone and isoamyl p-methoxy cinnamate.

In another preferred embodiment of the present invention, the sunscreen or daily care composition as defined above is further free of
titanium dioxide and zinc oxide;
oxybenzone and isoamyl p-methoxy cinnamate; and
parabens.

In another preferred embodiment of the present invention, the sunscreen or daily care composition as defined above is further free of
titanium dioxide and zinc oxide;
oxybenzone and isoamyl p-methoxy cinnamate;
parabens; and
phenoxyethanol.

In another preferred embodiment of the present invention, the sunscreen or daily care composition as defined above is further free of
titanium dioxide and zinc oxide;
oxybenzone and isoamyl p-methoxy cinnamate;
parabens; and
ethylhexyl salicylate and homosalate.

In another preferred embodiment of the present invention, the sunscreen or daily care composition as defined above is further free of
titanium dioxide and zinc oxide;
oxybenzone and isoamyl p-methoxy cinnamate;
parabens; and
emulsifier.

In another preferred embodiment of the present invention, the sunscreen or daily care composition as defined above is further free of
titanium dioxide and zinc oxide;
oxybenzone and isoamyl p-methoxy cinnamate;
parabens;
ethylhexyl salicylate and homosalate, and
phenoxyethanol.

In another preferred embodiment of the present invention, the sunscreen or daily care composition as defined above is further free of
titanium dioxide and zinc oxide;
oxybenzone and isoamyl p-methoxy cinnamate;
parabens;
emulsifier; and
phenoxyethanol.

In connection with the above preferred embodiments, it is to be understood that the sunscreen or daily care composition may be free of other substances or substance combinations than the substance combinations as listed above, e.g. 4-methoxybenzylidene camphor or benzophenone-3.

Further, in connection with the above preferred embodiments, it is to be understood that free of means that the composition does not comprise the substances as defined above. In particular, it is to be understood that the composition does not comprise each of the above-mentioned substances or combinations thereof in an overall amount of more than 0.8%, such as 0.7%, 0.6% or 0.5% by weight, based on the total weight of the composition. Preferred, it is to be understood that the composition does not comprise each of the above-mentioned substances or combinations thereof in an overall amount of more than 0.5% by weight.

In a more preferred embodiment of the present invention, the sunscreen or daily care composition does not comprise each of the above-mentioned substances or combinations thereof at all.

The following preferences regarding the amounts of the above defined UV filters or combinations thereof are relevant.

In one embodiment of the present invention, the sunscreen or daily care composition comprises hexyl 2-[4-(diethylamino)-2-hydroxybenzoyl]benzoate (INCI diethylamino hydroxybenzoyl hexyl benzoate) in an amount of from 1% to 10% by weight, based on the total weight of the composition. In a preferred embodiment, the sunscreen or daily care composition comprises hexyl 2-[4-(diethylamino)-2-hydroxybenzoyl]benzoate (INCI diethylamino hydroxybenzoyl hexyl benzoate) in an amount of from 1% to 8% by weight, based on the total weight of the sunscreen or daily care composition.

In another embodiment of the present invention, the sunscreen or daily care composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

In connection with the above embodiments, it is to be understood that the amounts of diethylamino hydroxybenzoyl hexyl benzoate and butyl methoxydibenzoylmethane are dependent from the ratio as defined above. In particular, it is to be understood that if for example diethylamino hydroxybenzoyl hexyl benzoate and butyl methoxydibenzoylmethane are present in a ratio of 2:1, preferred amounts of diethylamino hydroxybenzoyl hexyl benzoate are e.g. of from 1% to 10% by weight and preferred amounts of butyl methoxydibenzoylmethane are e.g. of from 1% to 5% by weight, based on the total weight of the sunscreen or daily care composition. In other words, this means that if the ratio is 2:1, diethylamino hydroxybenzoyl hexyl benzoate is present in an amount of 6% by weight and butyl methoxydibenzoylmethane is present in amount of 3% by weight, based on the total weight of the composition. The same applies for the other ratios as defined above.

In yet another embodiment of the present invention, the sunscreen or daily care composition comprises 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) in an amount of from 0.5% to 5% by weight, preferably in an amount of from 0.8% to 3% by weight, based on the total weight of the composition.

In yet another embodiment of the present invention, the sunscreen or daily care composition comprises 4,4',4"-(1,3,5-triazine-2,4,6-triyltriimino)tris-benzoic acid-tris(2-ethylhexyl)ester (INCI ethylhexyl triazone) in an amount of from 0.5% to 5% by weight, preferably in an amount of from 0.8% to 3% by weight, based on the total weight of the composition.

Further, in yet another embodiment of the present invention, the sunscreen or daily care composition comprises 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone) in an amount of from 0.5% to 5% by weight, preferably in an amount of from 0.8% to 3% by weight, based on the total weight of the composition.

In connection with the above embodiments, it is to be understood that if the composition comprises 4,4',4"-(1,3,5-triazine-2,4,6-triyltriimino)tris-benzoic acid-tris(2-ethylhexyl)ester (INCI ethylhexyl triazone) and 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone), the compounds are present in the composition in an overall amount of from 0.5% to 5% by weight, preferably in an overall amount of from 0.8% to 3% by weight, based on the total weight of the composition.

In yet another embodiment of the present invention, the sunscreen or daily care composition comprises the at least one organic particulate UV filter in an amount of from 0.5% to 10% by weight based on the total weight of the composition.

In a preferred embodiment of the present invention, the sunscreen or daily care composition comprises the at least one organic particulate UV filter in an amount of from 0.7% to 7% by weight based on the total weight of the composition.

In a particularly preferred embodiment of the present invention, the sunscreen or daily care composition comprises the at least one organic particulate UV filter in an amount of from 1% to 5% by weight based on the total weight of the composition.

In one embodiment of the present invention, the sunscreen or daily care composition has a sun protection factor (SPF) of at least 20. A person skilled in the art is aware that a high sun protection factor of a sunscreen or daily care composition depends on the UV filters present, in particular on the UV-B or broadband UV filters, which are present in the composition and on the respective amount of the UV filters. In connection with the sunscreen or daily care composition according to the present invention, it has surprisingly been found that a high sun protection factor of at least 20 can be achieved by the presence of the UV filters diethylamino hydroxybenzoyl hexyl benzoate, butyl methoxydibenzoylmethane, bis-ethylhexyloxyphenol methoxyphenyl triazine, ethylhexyl triazone and/or diethylhexyl-butamidotriazone, although the composition is free of octocrylene and ethylhexyl methoxy cinnamate. Furthermore, in connection with the above embodiment, it is to be understood that the sunscreen or daily care composition has an UVA protection factor, which is at least one third of the sun protection factor.

In another embodiment of the present invention, the sunscreen or daily care composition has a b* value of <25.

A person skilled in the art is aware, that the presence of certain UV filter changes the color of the sunscreen or daily care composition. In particular, due to the presence of oil soluble UVA filters sunscreen compositions reveal a more yellowish color. The color of a sunscreen or daily care composition can be expressed by its b* value. This value can be assessed based on the determination of the L*a*b* color space parameters. With this method, the color difference between several samples can be identified based on numerical values, as described in more detail below in the experimental section.

In this connection, it has surprisingly been found that the sunscreen or daily care composition as defined above, shows a bright color.

Further, in connection with the above embodiments, it is to be understood that the total weight of the sunscreen or daily care composition refers to the sunscreen composition as defined above, wherein the sunscreen composition may comprise at least one additive.

In one embodiment, the at least one additive is selected from the group consisting of emollients, viscosity regulators (thickeners), sensory enhancers, adjuvants, preservatives, perfumes and combinations thereof.

Preferred emollients include
  esters of linear or branched fatty acids with linear or branched fatty alcohols such as propylheptyl caprylate, coco caprylate, isopropyl myristate, ethylhexyl palmitate;
  esters of aromatic carboxylic acids with linear or branched fatty alcohols such as $C_{12}$-$C_{15}$-alkyl benzoate, ethylhexyl benzoate, phenethyl benzoate;
  dicarboxylic acid esters with linear or branched alcohols such as dibutyl adipate, dicaprylyl carbonate, diisopropyl sebacate;
  esters of hydroxycarboxylic acids with linear or branched fatty alcohols;
  esters of linear or branched fatty acids with polyhydric alcohol such as butylene glycol dicaprylate/dicaprate;
  mono-, di-, tri-glycerides based on $C_6$-$C_{18}$ fatty acids such as caprylic/capric triglycerides, coco glycerides;
  guerbet alcohols such as octyldodecynol;
  hydrocarbons such as hydrogenated polyisobutene, mineral oil, squalene, isohexadecane;
  ethers such as dicaprylyl ether;
  silicone derivatives (organomodified polysiloxanes) such as dimethylpolysiloxane, cyclic silicones.
Preferred thickeners include
  fatty alcohols such as cetyl alcohol, cetearyl alcohol, stearyl alcohol;
  fatty acids such as stearic acid;
  fatty acid esters such as myristyl stearate;
  waxes such as beeswax, carnauba wax, microcrystalline wax, ceresin, ozocerite;
  polysaccharides or derivatives such as xanthan gum, guar gum, agar gum, alginates, gellan gum, carraghenan;
  polyacrylates or homopolymers of reticulated acrylic acids or polyacrylamides such as carbomers, acrylate copolymers, acrylate/$C_{10}$-$C_{30}$-alkyl acrylate crosspolymer, acrylate/beheneth-25 methacrylate copolymer;
  silicate derivatives such as magnesium silicates;
  cellulose derivatives such as hydroxypropyl cellulose.
Preferred sensory enhancers include
  polyamide derivatives such as nylon-12;
  polymethyl methacrylates;
  silica;
  mica;
  polymethylsilsesquioxane;
  polyethylene;
  starch derivatives such as aluminum starch octenylsuccinate;
  dimethicone derivatives;
  boron nitride;
  HDI/trimethylol hexyllactone crosspolymer.
Preferred adjuvants include
  tocopherol derivatives;
  retinol derivatives;
  ascorbic acid derivatives;
  bisabolol;
  allantoin;
  panthenol;
  chelating agents (EDTA, EDDS, EGTA, phytic acid, piroctone olamine);
  ethylhexyl glycerin;
  caprylyl glycol;
  hydroxyacetophenone;
  caprylhydroxymic acid;
  propellants such as propane, butane, isobutene, dimethyl ether;
  styrene/PVP or styrene acrylamide copolymers;
  insect repellants such as butylacetylaminopropionate.

Preferred preservatives include
  benzyl alcohol;
  zingerone.

In one embodiment of the present invention, the sunscreen or daily care composition comprises perfume.

In a preferred embodiment of the present invention, the sunscreen or daily care composition comprises perfume selected from the group consisting of limonene, citral, linalool, alpha-isomethylionon, geraniol, citronellol, 2-isobutyl-4-hydroxy-4-methyltetrahydropyrane, 2-tert.-pentylcyclohexylacetate, 3-methyl-5-phenyl-1-pentanol, 7-acetyl-1,1,3,4,4,6-hexamethyltetraline, adipine acid diester, alpha-amylcinnamaldehyde, alpha-methylionon, amyl C butylphenylmethylpropionalcinnamal, amylsalicylate, amylcinnamylalcohol, anisalcohol, benzoin, benzylalcohol, benzylbenzoate, benzylcinnamate, benzylsalicylate, bergamot oil, bitter orange oil, butylphenylmethylpropioal, cardamom oil, cedrol, cinnamal, cinnamylalcohol, citronnellylmethylcrotonate, lemon oil, coumarin, diethylsuccinate, ethyllinalool, eugenol, evernia furfuracea extracte, evernia prunastri extracte, farensol, guajak wood oil, hexylcinnamal, hexylsalicylate, hydroxycitronellal, lavender oil, lemon oil, linaylacetate, mandarine oil, menthyl PCA, methylheptenone, nutmeg oil, rosemary oil, sweet orange oil, terpineol, tonka bean oil, triethylcitrate, vanillin and combinations thereof.

In connection with the at least one perfume present in the sunscreen or daily care composition, it has surprisingly been found that in case the composition comprises a UV filter in combination with a perfume, oxidative degeneration is reduced. In particular, it has surprisingly been found that the UV filter DHHB and BMDBM in the presence of at least one perfume reduce the oxidative degeneration.

In connection with the above embodiments, it is to be understood that if the sunscreen composition comprises two or more additives, combinations of the additives as defined above are also part of the invention.

In connection with the above embodiments, it is to be understood that the sunscreen composition may further comprise water.

In case water is present in the sunscreen or daily care composition it is to be understood that it is preferably present in an amount of more than 5% by weight, based on the total weight of the composition. Further, it is to be understood that in case water is present in the sunscreen composition, the sunscreen composition can be an oil in water emulsion (O/W emulsion), a water in oil emulsion (W/O emulsion), a gel cream or an oil in gel.

In one embodiment of the present invention, the sunscreen or daily care composition can be provided in different forms, e.g. gels, creams, oils, lotions or in the form of a sprayable product. In a preferred embodiment of the present invention, the sunscreen or daily care composition is provided in the form of a cream or a sprayable product. In a particularly preferred embodiment of the present invention, the sunscreen or daily care composition as defined above is provided in the form of a sprayable product.

In connection with the above preferred and particularly preferred embodiments, it is to be understood that depending on the form, in which the sunscreen or daily care composition is provided, further additives are added to the composition. Furthermore, in connection with the above preferred embodiments, it is to be understood that the term sprayable product refers to any formulation, which can be provided in a form that is sprayable not depending on the viscosity of the formulation, e.g. creams which can be provided in a sprayable form.

In another aspect, the present invention relates to the use of a sunscreen or daily care composition as defined above to reduce sand adhesion on the skin.

A person skilled in the art is aware, that sunscreen or daily care compositions can leave a sticky film on the skin after the sunscreen or daily care composition is applied. However, a sticky film leads to a higher adhesion of sand on the skin, which leaves an unpleasant feeling for the consumer.

Therefore, it has surprisingly been found that the sunscreen or daily care composition as defined above according to the present invention can be used to reduce sand adhesion on the skin.

In another aspect, the present invention thus relates to the use of a sunscreen or daily care composition as defined above for the administration to sensitive skin.

In one embodiment of the use of the present invention, the sunscreen or daily care composition is applied to the skin in different forms, e.g. gels, creams, oils, lotions or in the form of a sprayable product.

In a preferred embodiment of the use of the present invention, the sunscreen or daily care composition is provided in the form of a cream or a sprayable product. In a particularly preferred embodiment of the use of the present invention, the sunscreen or daily care composition as defined above is provided in the form of a sprayable product.

In a particularly preferred embodiment of the use of the present invention, the sunscreen or daily care composition as defined above is applied to sensitive skin. In this connection, sensitive skin is defined as skin of which the natural barrier function is weakened and has broken due to a trigger. Possible triggers are cold weather, extremely hot water, emulsifier or preservatives, which are often included in sunscreen or daily care compositions.

Thus, in a preferred embodiment of the use of the present invention, a sunscreen or daily care composition as defined above, which is free of emulsifier, is applied. In this connection, it is to be understood that due to the absence of an emulsifier these compositions are especially suitable and preferred for the administration to sensitive skin. Therefore, the inventors of the present invention have surprisingly found that emulsifier free, homogeneous and stable sunscreen or daily care composition can be prepared, which are particularly preferred for the administration to sensitive skin.

In connection with the above embodiments, it is to be understood that the sunscreen or daily care composition is administered on the skin, in particular on sensitive skin, in order to protect the sensitive skin from UV radiation.

The present invention is further illustrated by the following examples.

EXAMPLES

Process of Manufacture of Sunscreen Compositions

The ingredients of part A, as well as the ingredients of part B as provided below in Tables 1.1, 1.2, 1.3 and 1.4 for each tested sunscreen composition were combined and heated to 80° C. respectively, wherein part A was added to part B under stirring and was further homogenized. Subsequently, the sunscreen composition was cooled down to room temperature under stirring. If present, part C was added and the pH of each composition was adjusted to 6.5-7.00 with NaOH.

All amounts referred to in the following tables refer to the respective amounts in % by weight, based on the total weight of the composition.

Sunscreen Compositions

TABLE 1.1

| Ingredient (Trade Name) | Comparative composition 1a | Comparative composition 1b | Comparative composition 1c |
|---|---|---|---|
| Part A | | | |
| Dibutyl adipate (Cetiol B) | 15.00 | 15.00 | 10.00 |
| $C_{12}$-$C_{15}$ alkyl benzoate (Cetiol AB) | 10.00 | 10.00 | 10.00 |
| Stearyl alcohol (Lanette 18) | 2.50 | 2.50 | 2.50 |
| Preservative | 1.00 | 1.00 | 1.00 |
| BMDBM | 4.00 | 4.00 | 4.00 |
| DHHB (Uvinul A Plus) | — | — | 2.00 |
| BEMT (Tinosorb S) | 1.00 | 1.00 | 1.00 |
| OCR (Uvinul N539T) | 10.00 | — | — |
| Part B | | | |
| Water | qsp 100% | qsp 100% | qsp 100% |
| Glycerin | 2.00 | 2.00 | 2.00 |
| Disodium EDTA | 0.20 | 0.20 | 0.20 |
| Acrylates/Beheneth-25 methacrylate copolymer (Tinovis GTC) | 2.00 | 2.00 | 2.00 |
| Xanthan Gum (Rheocare XGN) | 0.50 | 0.50 | 0.50 |

TABLE 1.2

| Ingredient (Trade Name) | Composition 2 | Composition 3 | Composition 4 |
|---|---|---|---|
| Part A | | | |
| Dibutyl adipate (Cetiol B) | 15.00 | 15.00 | 15.00 |
| $C_{12}$-$C_{15}$ alkyl benzoate (Cetiol AB) | 10.00 | 10.00 | 10.00 |
| Stearyl alcohol (Lanette 18) | 2.50 | 2.50 | 2.50 |
| Preservative | 1.00 | 1.00 | 1.00 |
| BMDBM | 4.00 | 4.00 | 4.00 |
| DHHB (Uvinul A Plus) | 4.00 | 6.00 | 8.00 |
| BEMT (Tinosorb S) | 1.00 | 1.00 | 1.00 |
| OCR (Uvinul N539T) | — | — | — |
| Part B | | | |
| Water | qsp 100% | qsp 100% | qsp 100% |
| Glycerin | 2.00 | 2.00 | 2.00 |
| Disodium EDTA | 0.20 | 0.20 | 0.20 |
| Acrylates/Beheneth-25 methacrylate copolymer (Tinovis GTC) | 2.00 | 2.00 | 2.00 |
| Xanthan Gum (Rheocare XGN) | 0.50 | 0.50 | 0.50 |

TABLE 1.3

| Ingredient (Trade Name) | Composition 5 |
|---|---|
| Part A | |
| Dibutyl adipate (Cetiol B) | 15.00 |
| $C_{12}$-$C_{15}$ alkyl benzoate (Cetiol AB) | 10.00 |
| Stearyl alcohol (Lanette 18) | 2.50 |
| Preservative | 1.00 |
| BMDBM | 4.00 |
| DHHB (Uvinul A Plus) | 10.00 |
| BEMT (Tinosorb S) | 1.00 |
| OCR (Uvinul N539T) | — |
| Part B | |
| Water | qsp 100% |
| Glycerin | 2.00 |
| Disodium EDTA | 0.20 |

TABLE 1.3-continued

| Ingredient (Trade Name) | Composition 5 |
| --- | --- |
| Acrylates/Beheneth-25 methacrylate copolymer (Tinovis GTC) | 2.00 |
| Xanthan Gum (Rheocare XGN) | 0.50 |

TABLE 1.4

| Ingredient (Trade Name) | Comparative composition 2a | Comparative composition 2b | Composition 6 |
| --- | --- | --- | --- |
| Part A | | | |
| Dibutyl adipate (Cetiol B) | 10.00 | 10.00 | 10.00 |
| $C_{12}$-$C_{15}$ alkyl benzoate (Cetiol AB) | 10.00 | 10.00 | 10.00 |
| Stearyl alcohol (Lanette 18) | 2.50 | 2.50 | 2.50 |
| BMDBM | 3.00 | 3.00 | 3.00 |
| DHHB (Uvinul A Plus) | — | — | 5.00 |
| BEMT (Tinosorb S) | 1.00 | 1.00 | 1.00 |
| Part B | | | |
| Water | qsp 100% | qsp 100% | qsp 100% |
| Glycerin | 2.00 | 2.00 | 2.00 |
| Disodium EDTA (EDTA BD) | 0.20 | 0.20 | 0.20 |
| Acrylates/Beheneth-25 methacrylate copolymer (Tinovis GTC UP) | 2.00 | 2.00 | 2.00 |
| Xanthan Gum (Rheocare XGN) | 0.50 | 0.50 | 0.50 |
| Part C | | | |
| MBBT* (Tinosorb M) | 5.00 | — | — |

*The amount refers to active matter, 5% of MBBT corresponds to 10% of the commercial product Tinosorb M.

Recovery Measurements on Photo Stability of BMDBM

The sunscreen or UV filter compositions as defined above are applied on roughened quartz plates (2 µl/cm²). Plates are irradiated using Atlas CPS device at different duration times (MED=Minimal Erythema Dose):

0 h (0 MED, no irradiation)

1 h (5 MED), 2 h (10 MED), 4 h (28 MED).

In total, four plates are prepared for each irradiation condition. After irradiation, each plate is rinsed off with tetrahydrofuran. The rinsing solution is further analyzed via HPLC to determine the recovery of BMDBM.

TABLE 2.1

| | Comparative composition 1a | Comparative composition 1b | Comparative composition 1c |
| --- | --- | --- | --- |
| 0 MED | 100% | 100% | 100% |
| 5 MED | 98% | 58% | 62% |
| 10 MED | 89% | 31% | 37% |
| 20 MED | 83% | 12% | 14% |

TABLE 2.2

| | Composition 2 | Composition 3 |
| --- | --- | --- |
| 0 MED | 100% | 100% |
| 5 MED | 79% | 87% |

TABLE 2.2-continued

| | Composition 2 | Composition 3 |
| --- | --- | --- |
| 10 MED | 62% | 75% |
| 20 MED | 33% | 52% |

TABLE 2.3

| | Composition 4 | Composition 5 |
| --- | --- | --- |
| 0 MED | 100% | 100% |
| 5 MED | 86% | 97% |
| 10 MED | 73% | 77% |
| 20 MED | 55% | 61% |

TABLE 2.4

| | Comparative composition 2a | Comparative composition 2b | Composition 6 |
| --- | --- | --- | --- |
| 0 MED | 100% | 100% | 100% |
| 5 MED | 68% | 55% | 82% |
| 10 MED | 43% | 26% | 63% |
| 20 MED | 21% | 11% | 41% |

Recovery Measurements on Photo Stability of BEMT

The sunscreen or UV filter compositions as defined above are applied on roughened quartz plates (2 µl/cm²). Plates are irradiated using Atlas CPS device at different duration times (MED=Minimal Erythema Dose):

0 h (0 MED, no irradiation)

1 h (5 MED), 2 h (10 MED), 4 h (20 MED).

In total, four plates are prepared for each irradiation condition. After irradiation, each plate is rinsed off with tetrahydrofuran. The rinsing solution is further analyzed via HPLC to determine the recovery of BEMT.

TABLE 3.1

| | Comparative composition 1a | Comparative composition 1b | Comparative composition 1c |
| --- | --- | --- | --- |
| 0 MED | 100% | 100% | 100% |
| 5 MED | 103% | 93% | 92% |
| 10 MED | 98% | 86% | 89% |
| 20 MED | 100% | 76% | 76% |

A Person Skilled in the Art is Aware that Data Above 100% after Irradiation are Due to Common Measurement Fluctuations.

TABLE 3.2

| | Composition 2 | Composition 3 |
| --- | --- | --- |
| 0 MED | 100% | 100% |
| 5 MED | 99% | 101% |
| 10 MED | 102% | 104% |
| 20 MED | 95% | 102% |

A Person Skilled in the Art is Aware that Data Above 100% after Irradiation are Due to Common Measurement Fluctuations.

TABLE 3.3

|  | Composition 4 | Composition 5 |
|---|---|---|
| 0 MED | 100% | 100% |
| 5 MED | 98% | 106% |
| 10 MED | 95% | 98% |
| 20 MED | 95% | 97% |

A Person Skilled in the Art is Aware that Data Above 100% after Irradiation are Due to Common Measurement Fluctuations.

TABLE 3.4

|  | Comparative composition 2a | Comparative composition 2b | Composition 6 |
|---|---|---|---|
| 0 MED | 100% | 100% | 100% |
| 5 MED | 98% | 93% | 97% |
| 10 MED | 92% | 84% | 92% |
| 20 MED | 90% | 78% | 92% |

Measurement of Interfacial Tension (Polarity Index)

Interfacial tension of the respective emollients as listed below was measured using a Tensimat Densimat TD2000.

TABLE 4.1

|  |  | polarity index [mN/m] |
|---|---|---|
| polarity index >30 mN/m (reference emollients) | hydrogenated polyisobutene | 45 |
|  | mineral oil | 43 |
|  | cyclopentasiloxane | 32 |
| polarity index <30 mN/m | octyldodecanol | 25 |
|  | butylene glycol dicaprylate/dicaprate | 22 |
|  | C12-15 alkyl benzoate | 22 |
|  | caprylic capric triglyceride | 21 |
|  | propylene glycol dicaprylate/dicaprate | 20 |
|  | diisopropyl sebacate | 19 |
|  | phenethyl benzoate | 19 |
|  | dibutyl adipate | 14 |
|  | diisopropyl adipate | 12 |
|  | triethyl citrate | 7 |
|  | tributyl citrate | 10 |

UV Filter Performance

The wavelength of maximum absorbance (λmax) is an indicator to describe the performance of a UV filter molecule. It gives the wavelength at which the absorbance is at maximum. For a UVA filter, the wavelength of maximum absorbance should be close to 359 nm that corresponds to the apex of the PPD (persistent pigment darkening) effectiveness spectrum. The PPD effectiveness spectrum corresponds to the multiplication of the PPD (persistent pigment darkening) action spectrum with the light intensity (see ISO 24443).

The UV transmission spectrum of each UV filter-emollient mixture was measured from 290 to 400 nm using a UV/Vis spectrophotometer Perkin Elmer Lambda 25. Three stock solutions with a concentration of 1 mM of UV filter were prepared for each mixture. Further, three dilutions of each stock solution were prepared resulting in nine measurements in total per UV filter-emollient solution. Then, all solutions were filled in UV transparent quartz cuvette of 1 cm optical path-length for UV Transmission measurements.

λMax Values of BMDBM

TABLE 4.2

|  |  | λmax values [nm] (BMDBM) |
|---|---|---|
| polarity index >30 mN/m (reference emollients) | mineral oil | 355 |
|  | hydrogenated polyisobutene | 354 |
|  | cyclomethicone | 350 |
| polarity index <30 mN/m | diisopropyl adipate | 357 |
|  | isopropyl myristate | 357 |
|  | dicaprylyl carbonate | 357 |
|  | dibutyl adipate | 358 |
|  | caprylic capric triglyceride | 358 |
|  | C12-15 alkyl benzoate | 359 |
|  | phenethyl benzoate | 362 |
|  | diisopropyl sebacate | 357 |
|  | octyldodecanol | 357 |
|  | triethyl citrate | 359 |
|  | tributyl citrate | 359 |

λMax Values of DHHB

TABLE 4.3

|  |  | λmax values [nm] (DHHB) |
|---|---|---|
| polarity index >30 mN/m (reference emollients) | hydrogenated polyisobutene |  |
|  | cyclomethicone | 345 |
|  | mineral oil | 346 |
| polarity index <30 mN/m | phenethyl benzoate | 355 |
|  | dibutyl adipate | 351 |
|  | C12-15 alkyl benzoate | 351 |
|  | diisopropyl adipate | 351 |
|  | butylene glycol dicaprylate/dicaprate | 350 |
|  | caprylic capric triglyceride | 350 |
|  | diisopropyl sebacate | 350 |
|  | octyldodecanol | 349 |
|  | triethyl citrate | 353 |
|  | tributyl citrate | 352 |

Solubility Measurements 0.02 g of UV Filter are added to 2 ml of the respective emollient as displayed below, previously filled into a 20 ml vial with cap. The vial is placed in a thermostated water bath (25° C.) and the blend is stirred for seven days. If the tested UV-filter is fully soluble, additional filter is added until precipitation is observed. After seven days, the sample is centrifuged for 30 minutes at 13000 rpm. If the supernatant is turbid, it is filtered through a 0.2 μm non steril Membrex 25 PET filter. Prior to the measurement, the samples were either diluted with a suitable solvent, or, in case of lower concentrations measured without further dilution in quartz cuvettes of 1 cm optical path-length. The concentration of UV-filter is then determined with UV/Vis-spectroscopy using a Perkin Elmer Lambda 20 device (according to Method A in Herzog B., Giesinger J., Schnyder M., SOFW Journal, 2013, 139 (7), pages 7-14).

TABLE 4.4

|  |  | solubility [%] (BMDBM) |
|---|---|---|
| polarity index >30 mN/m (reference emollients) | mineral oil | <1 |
|  | hydrogenated polyisobutene | <1 |
|  | cyclomethicone | <1 |
|  | diisopropyl adipate | 10 |
| polarity index <30 mN/m | dibutyl adipate | 18 |
|  | caprylic capric triglyceride | 12 |
|  | C12-15 alkyl benzoate | 14 |
|  | phenethyl benzoate | 25 |
|  | diisopropyl sebacate | 16 |
|  | octyldodecanol | 2 |
|  | triethyl citrate | 15 |
|  | tributyl citrate | 18 |

TABLE 4.5

|  |  | solubility [%] (DHHB) |
|---|---|---|
| polarity index >30 mN/m (reference emollients) | mineral oil | <1 |
|  | hydrogenated polyisobutene | <1 |
|  | cyclomethicone | <1 |
| polarity index <30 mN/m | phenethyl benzoate | 57 |
|  | dibutyl adipate | 31 |
|  | C12-15 alkyl benzoate | 22 |
|  | diisopropyl adipate | 21 |
|  | butylene glycol dicaprylate/dicaprate | 23 |
|  | propylene glycol dicaprylate/dicaprate | 22 |
|  | caprylic capric triglyceride | 14 |
|  | diisopropyl sebacate | 41 |
|  | octyldodecanol | 2.5 |
|  | triethyl citrate | 29 |
|  | tributyl citrate | 29.4 |

Sand Adhesion Test

The ingredients of part A, as well as the ingredients of part B as provided below in Table 5 for each tested sunscreen composition were combined and heated to 80° C. respectively, wherein part A was added to part B under stirring and was further homogenized. Subsequently, the sunscreen composition was cooled down to room temperature under stirring. Parts C and 0 were added and the pH of each composition was adjusted to 6.5-7.00 with NaOH.

TABLE 5

| Ingredient (Trade Name) | Comparative Composition 3 | Composition 7 | Composition 8 | Composition 9 |
|---|---|---|---|---|
| Part A | | | | |
| Stearyl phosphate | 5.00 | 5.00 | 5.00 | 5.00 |
| Phenethyl benzoate | 3.00 | 3.00 | 3.00 | 3.00 |
| Triisodecyl trimellitate | 3.00 | 3.00 | 3.00 | 3.00 |
| Dimethyl capramide | 1.00 | 1.00 | 1.00 | 1.00 |
| Tricontanyl PVP | 1.00 | 1.00 | 1.00 | 1.00 |
| Ethoxydiglycol oleate | 1.50 | 1.50 | 1.50 | 1.50 |
| Squalane | 3.00 | 3.00 | 3.00 | 3.00 |
| C12-15 alkyl benzoate (Cetiol AB) | 2.00 | 2.00 | 2.00 | 2.00 |
| Glyceryl stearate | 2.00 | 2.00 | 2.00 | 2.00 |
| Cetyl alcohol (Lanette 16) | 2.00 | 2.00 | 2.00 | 2.00 |
| Bis-ethylhexyloxyphenol Methoxyphenyl Triazine (Tinosorb S) | 2.00 | 2.00 | 2.00 | 5.00 |
| Propanedioic acid, 2-[(4-methoxyphenyl)methylene]-, 1,3-bis((2-methylbutyl) ester | 10.00 | | | |
| Diethylhexyl Butamino Triazone | | 8.00 | 4.00 | |
| Diethylamino Hydroxy-benzoyl Hexyl Benzoate (Uvinul A Plus) | 4.00 | 4.00 | 4.00 | 4.00 |
| Ethylhexyl Triazone (Uvinul T150) | 2.00 | | 4.00 | 5.00 |
| Butyl Methoxydibenzoyl-methane | 3.00 | 3.00 | 3.00 | 3.00 |
| Part B | | | | |
| Aqua | qsp 100% | qsp 100% | qsp 100% | qsp 100% |
| Steareth-10 allyl ether/acrylates | 0.50 | 0.50 | 0.50 | 0.50 |
| Glycerine | 2.50 | 2.50 | 2.50 | 2.50 |
| Diazolidinyl urea (and) iodopropynyl butylcarbamate | 0.15 | 0.15 | 0.15 | 0.15 |

TABLE 5-continued

| Ingredient (Trade Name) | Comparative Composition 3 | Composition 7 | Composition 8 | Composition 9 |
|---|---|---|---|---|
| Sodium Stearoyl Gluta | 0.70 | 0.70 | 0.70 | 0.70 |
| Sclerotium Gum | 0.10 | 0.10 | 0.10 | 0.10 |
| Part C | | | | |
| Cyclopentasiloxane (and) dimethiconol | 1.50 | 1.50 | 1.50 | 1.50 |
| Triethanolamine | 1.85 | 1.85 | 1.85 | 1.85 |
| Citric acid (and) silver citrate | 0.10 | 0.10 | 0.10 | 0.10 |
| Part D | | | | |
| Methylene Bis-Benzotria-zolyl Tetramethylbutyl-phenol* | 3.00 | 3.00 | 3.00 | 3.00 |
| SPF cal. | 52 | 52 | 53 | 53 |

*The amount refers to active matter, 3% MBBT corresponds to 6% of the commercial product Tinosorb M Comparative Composition 3 and Compositions 7, 8 and 9 have been tested for their performance to prevent or at least minimize sand adhesion on the skin after application of the sunscreen composition. The following method has been used:

50 mg of the test formulation was applied on PMMA plates (Helioscreen) with a dimension of 5.0 cm×5.0 cm by manual application as homogeneous as possible. The plates were placed for 15 minutes in the dark to allow water evaporation and equilibration of the plate to achieve the film formation before further processing. After equilibration period, each single plate was weighted with an analytical balance. The sample was covered with 10 g of sand (ref. 1.07711.1000 seesand, Merck KGaA). This amount allows a coverage in excess of the entire PMMA plate. Afterwards, the plate was put from the horizontal position in the vertical position equaling a 90° C. turn and kept for 5 seconds in the vertical position. The same step was repeated for each side of the plate. The plate with the remaining stuck sand was weighed again and the amount of stuck sand calculated according to the following formula:

Sand adhered on the plate (mg)=plate after sand contact (mg)−sunscreen-covered plate (mg)

The sand adhesion rates for each composition are as shown in Table 6.

TABLE 6

| | Comparative Composition 3 | Composition 7 | Composition 8 | Composition 9 |
|---|---|---|---|---|
| Sand adhesion tests | 0.527 | 0.5239 | 0.4978 | 0.5194 |
| | 0.5437 | 0.5388 | 0.5122 | 0.5232 |
| | 0.5581 | 0.5428 | 0.5063 | 0.5399 |
| | 0.5599 | 0.5138 | 0.5142 | 0.4891 |
| | 0.5493 | 0.5155 | 0.4947 | 0.5012 |
| Average sand adhesion | 0.548 | 0.527 | 0.505 | 0.515 |

Comparative Composition 3 shows a stronger stickiness to sand than the inventive Compositions 7, 8 and 9.

Color Test

The ingredients of part A, as well as the ingredients of part B as provided below in Table 7 for each tested sunscreen composition were combined and heated to 80° C. respectively, wherein part A was added to part B under stirring and was further homogenized. Subsequently, the sunscreen composition was cooled down to room temperature under stirring. Parts C and 0 were added and the pH of each composition was adjusted to 6.5-7.00 with NaOH.

TABLE 7

| Ingredient (Trade Name) | Comparative Composition 4 | Composition 10 | Composition 11 |
|---|---|---|---|
| Part A | | | |
| Octyldodecanol (Eutanol G) | 4.00 | 4.00 | 4.00 |
| caprylic/capric triglycerides | 1.00 | 1.00 | 1.00 |
| glyceryl stearate | 1.00 | 1.00 | 1.00 |
| hydrogenated coco-glycerides | 1.00 | 1.00 | 1.00 |
| ethylhexyl cocoate | 4.00 | 4.00 | 4.00 |
| sodium stearoyl glutamate (Emulgin SG) | 0.30 | 0.30 | 0.30 |
| silica dimethyl silylate | 2.00 | 2.00 | 2.00 |
| Bis-ethylhexyloxyphenol Methoxyphenyl Triazine (Tinosorb S) | 1.00 | 1.00 | 1.00 |
| Diethylhexyl Butamino Triazone | 1.00 | 1.00 | 5.00 |
| Diethylamino Hydroxybenzoyl | | | |

TABLE 7-continued

| Ingredient (Trade Name) | Comparative Composition 4 | Composition 10 | Composition 11 |
|---|---|---|---|
| Hexyl Benzoate (Uvinul A Plus) | 5.00 | 5.00 | 5.00 |
| Ethylhexyl Triazone (Uvinul T150) | 4.00 | 4.00 | |
| Butyl Methoxydibenzoylmethane | 3.50 | 3.50 | 3.50 |
| Titanium dioxide (and) Triethoxycaprylylsilane | 1.50 | | |
| Homosalate | 7.00 | 7.00 | 7.00 |
| Ethylhexyl Salicylate | 3.50 | 3.50 | 3.50 |
| Part B | | | |
| Aqua | qsp 100% | qsp 100% | qsp 100% |
| Sodium hydroxyde | 0.025 | 0.025 | 0.025 |
| Xanthan gum | 0.50 | 0.50 | 0.50 |
| Acrylates/C10-30 alkyl acrylate crosspolymer | 0.10 | 0.10 | 0.10 |
| Part C | | | |
| Methylene Bis-Benzotriazolyl Tetramethylbutyl phenol * | 1.50 | 1.50 | |
| Part D | | | |
| Phenoxyethanol | 0.60 | 0.60 | 0.60 |
| Alcohol denat | 6.00 | 6.00 | 6.00 |
| SPF cal. | 40 | 42 | 42 |

* The amount refers to active matter, 1,5% MBBT corresponds to 3% of the commercial product Tinosorb M Comparative Composition 4 and Compositions 10 and 11 have been tested for their color. The principle is that the brighter the color of the product is, the more the product is accepted by the consumer. The following method has been used:

The color of a cosmetic sunscreen formulation is assessed based on the determination of the L*a*b* color space parameters. With this method, the color difference between several samples can be identified based on numerical values. In the L*a*b* system, L corresponds to the lightness, a to the red/green coordinate and b to the yellow/blue coordinate. The advantage of this method is that it is not dependent on the device used for the measurements. The formulation to be measured is filled into transparent petri dish (58×15 mm). The lid is placed on the petri dish carefully to avoid any air bubbles underneath the lid. L*a*b* parameters are measured of the sunscreen containing petri dish with a Remission Spectrometer Datacolor SF400 (light D65, observer 10°). Sunscreens very often show a yellow color, which is not desired by the end consumer. To increase the consumer compliance, a sunscreen should be less yellow as possible. Therefore, the parameter b* is taken for the evaluation of the yellow color of the formulation, the higher the b* value, the higher the measured yellow tone.

The evaluation of the color of Comparative Composition 4 and Compositions 9 and 10 is shown in Table 8 below.

TABLE 8

| | Comparative Composition 4 | Composition 10 | Composition 11 |
|---|---|---|---|
| b* value | 28.43 | 18.98 | 20.47 |

As can been seen from the b* value, the color of Comparative Composition 4 is much more yellow than the color of the inventive Compositions 10 and 11.

In a preferred embodiment, the present invention relates to the following further items.
1. A sunscreen or daily care composition comprising
   (i) hexyl 2-[4-(diethylamino)-2-hydroxybenzoyl]benzoate (INCI diethylamino hydroxybenzoyl hexyl benzoate); and
   (ii) 1-(4-(1,1-dimethylethyl)phenyl)-3-(4-methoxyphenyl)propane-1,3-dione (INCI butyl methoxydibenzoylmethane); and
   (iii) 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine); and
   (iv) 4,4',4"-(1,3,5-triazine-2,4,6-triyltriimino)tris-benzoic acid-tris(2-ethylhexyl)ester (INCI ethylhexyl triazone) and/or 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone),
wherein the composition is free of ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate); and wherein the composition comprises (i) to (ii) in a ratio of larger or equal to 0.8.
2. The sunscreen or daily care composition according to item 1, wherein the composition comprises (i) hexyl 2-[4-(diethylamino)-2-hydroxybenzoyl]benzoate (INCI diethylamino hydroxybenzoyl hexyl benzoate) and (ii) 1-(4-(1,1-dimethylethyl)phenyl)-3-(4-methoxyphenyl)propane-1,3-dione (INCI butyl methoxydibenzoylmethane) in a ratio of larger or equal to 1.
3. The sunscreen or daily care composition according to item 1 or 2, wherein the composition comprises (i) hexyl 2-[4-(diethylamino)-2-hydroxybenzoyl]benzoate (INCI diethylamino hydroxybenzoyl hexyl benzoate) and (ii) 1-(4-(1,1-dimethylethyl)phenyl)-3-(4-methoxyphenyl)propane-1,3-dione (INCI butyl methoxydibenzoylmethane) in a ratio of from 1:1 to 10:1, preferably in a ratio of from 1:1 to 5:1, more preferably in a ratio of from 1:1 to 2:1 and even more preferably in a ratio of from 1:1 to 1.5:1.

4. The sunscreen or daily care composition according to any one of items 1 to 3, wherein the composition is free of titanium dioxide, and zinc oxide.

5. The sunscreen or daily care composition according to any one of items 1 to 4, wherein the composition does not comprise 2-hydroxy-4-methoxybenzophenone (INCI oxybenzone) and isoamyl-4-methoxycinnamate (INCI isoamyl-p-methoxy cinnamate).

6. The sunscreen or daily care composition according to any one of items 1 to 5, wherein the composition is free of parabens.

7. The sunscreen or daily care composition according to any one of items 1 to 6, wherein the composition is provided in the form of a sprayable product.

8. The sunscreen or daily care composition according to any one of items 1 to 7, wherein the composition is free of emulsifier.

9. The sunscreen or daily care composition according to any one of items 1 to 8, wherein the composition is free of phenoxyethanol.

10. The sunscreen or daily care composition according to any one of items 1 to 9, wherein (iii) is an oil soluble UV filter or wherein (iii) is 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) dissolved in a polymer matrix to be dispersible in water.

11. The sunscreen or daily care composition according to any one of items 1 to 10, wherein the composition comprises hexyl 2-[4-(diethylamino)-2-hydroxybenzoyl]benzoate (INCI diethylamino hydroxybenzoyl hexyl benzoate) in an amount of from 1% to 10% by weight, based on the total weight of the composition.

12. The sunscreen or daily care composition according to any one of items 1 to 11, wherein the composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

13. The sunscreen or daily care composition according to any one of items 1 to 12, wherein the composition comprises 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) in an amount of from 0.5% to 5% by weight, preferably in an amount of from 0.8% to 3% by weight, based on the total weight of the composition.

14. The sunscreen or daily care composition according to any one of items 1 to 13, wherein the composition comprises 4,4',4''-(1,3,5-triazine-2,4,6-triyltriimino)tris-benzoic acid-tris(2-ethylhexyl)ester (INCI ethylhexyl triazone) in an amount of from 0.5% to 5% by weight, preferably in an amount of from 0.8% to 3% by weight, based on the total weight of the composition.

15. The sunscreen or daily care composition according to any one of items 1 to 14, wherein the composition comprises 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone) in an amount of from 0.5% to 5% by weight, preferably in an amount of from 0.8% to 3% by weight, based on the total weight of the composition.

16. The sunscreen or daily care composition according to any one of items 1 to 15, wherein the composition has a sun protection factor (SPF) of at least 20.

17. Use of a sunscreen or daily care composition as defined in any one of items 1 to 15 for the administration to sensitive skin.

The invention claimed is:

1. A sunscreen or daily care composition comprising
(i) hexyl 2-[4-(diethylamino)-2-hydroxybenzoyl]benzoate (INCI diethylamino hydroxybenzoyl hexyl benzoate); and
(ii) 1-(4-(1,1-dimethylethyl)phenyl)-3-(4-methoxyphenyl)propane-1,3-dione (INCI butyl methoxydibenzoylmethane); and
(iii) 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine); and
(iv) 4,4',4''-(1,3,5-triazine-2,4,6-triyltriimino)tris-benzoic acid-tris(2-ethylhexyl)ester (INCI ethylhexyl triazone) and/or 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone); and
(v) at least one organic particulate UV filter,
wherein the composition is free of ethylhexyl-2-cyano-3,3-diphenyl-acrylate (INCI octocrylene), 2-ethylhexyl-(2E)-3-(4-methoxyphenyl)acrylate (INCI ethylhexyl methoxy cinnamate) and benzylidene malonates according to the following structures:

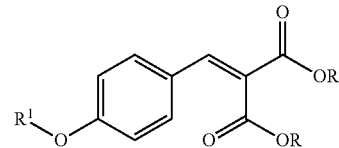

wherein
$R^1$ is methyl, ethyl, propyl or n-butyl;
if $R^1$ is methyl, then
R is tert butyl or a radical of formula

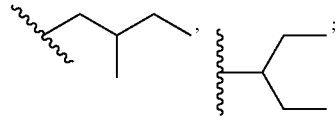

or a radical of formula

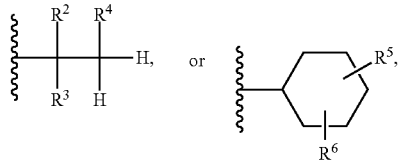

wherein
$R^2$ and $R^3$ are independently from each other hydrogen or methyl;
$R^4$ is methyl, ethyl or n-propyl;
$R^5$ and $R^6$ are independently from each other hydrogen or $C_1$-$C_3$-alkyl;
if $R^1$ is ethyl, propyl or n-butyl, then
R is isopropyl;

and wherein the composition comprises (i) to (ii) in a ratio of larger or equal to 0.8.

2. The sunscreen or daily care composition according to claim 1, wherein the composition comprises (i) hexyl 2-[4-(diethylamino)-2-hydroxybenzoyl]benzoate (INCI diethylamino hydroxybenzoyl hexyl benzoate) and (ii) 1-(4-(1,1-dimethylethyl)phenyl)-3-(4-methoxyphenyl)propane-1,3-dione (INCI butyl methoxydibenzoylmethane) in a ratio of larger or equal to 1.

3. The sunscreen or daily care composition according to claim 1, wherein the composition comprises (i) hexyl 2-[4-(diethylamino)-2-hydroxybenzoyl]benzoate (INCI diethylamino hydroxybenzoyl hexyl benzoate) and (ii) 1-(4-(1,1-dimethylethyl)phenyl)-3-(4-methoxyphenyl)propane-1,3-dione (INCI butyl methoxydibenzoylmethane) in a ratio of from 1:1 to 10:1.

4. The sunscreen or daily care composition according to claim 1, wherein the composition is free of titanium dioxide and zinc oxide.

5. The sunscreen or daily care composition according to claim 1, wherein the composition does not comprise 2-hydroxy-4-methoxybenzophenone (INCI oxybenzone) and isoamyl-4-methoxycinnamate (INCI isoamyl-p-methoxy cinnamate).

6. The sunscreen or daily care composition according to claim 1, wherein the composition is free of parabens.

7. The sunscreen or daily care composition according to claim 1, wherein the composition is provided in the form of a sprayable product.

8. The sunscreen or daily care composition according to claim 1, wherein the composition is free of emulsifier.

9. The sunscreen or daily care composition according to claim 1, wherein the composition is free of phenoxyethanol.

10. The sunscreen or daily care composition according to claim 1, wherein (iii) is an oil soluble UV filter or wherein (iii) is 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) dissolved in a polymer matrix to be dispersible in water.

11. The sunscreen or daily care composition according to claim 1, wherein the composition comprises hexyl 2-[4-(diethylamino)-2-hydroxybenzoyl]benzoate (INCI diethylamino hydroxybenzoyl hexyl benzoate) in an amount of from 1% to 10% by weight, based on the total weight of the composition.

12. The sunscreen or daily care composition according to claim 1, wherein the composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

13. The sunscreen or daily care composition according to claim 1, wherein the composition comprises 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) in an amount of from 0.5% to 5% by weight, based on the total weight of the composition.

14. The sunscreen or daily care composition according to claim 1, wherein the composition comprises 4,4',4''-(1,3,5-triazine-2,4,6-triyltriimino)tris-benzoic acid-tris(2-ethylhexyl)ester (INCI ethylhexyl triazone) in an amount of from 0.5% to 5% by weight based on the total weight of the composition.

15. The sunscreen or daily care composition according to claim 1, wherein the composition comprises 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl) ester (INCI diethylhexyl-butamidotriazone) in an amount of from 0.5% to 5% by weight, based on the total weight of the composition.

16. The sunscreen or daily care composition according to claim 1, wherein the at least one organic particulate UV filter is selected from the group consisting of 2,2'-methylene bis[6-(2H-benzotriazol-2-yl)-4-(1,1,3,3-tetramethylbutyl) phenol] (INCI methylene bis-benzotriazolyl tetramethylbutylphenol), 2,4,6-tris(biphenyl-4-yl)-1,3,5-triazine (INCI trisbiphenyl triazine),1,1'-(1,4-piperazinediyl)bis[1-[2-[4-(diethylamino)-2-hydroxybenzoyl]phenyl]-methanone (INCI bis-(diethylaminohydroxybenzoyl benzoyl) piperazine), 5,6,5',6'-tetraphenyl-3-3'-(1,4-phenylene)bis(1,2,4-triazine) (INCI phenylene bis-diphenyltriazine), micronized 1,4-di(benzoxazole-2'-yl)benzene and combinations thereof.

17. The sunscreen or daily care composition according to claim 1, wherein the composition has a sun protection factor (SPF) of at least 20.

18. The sunscreen or daily care composition according to claim 1, wherein the composition has a b* value of <25.

19. A method for reducing sand adhesion to skin by applying the sunscreen or daily care composition according to claim 1 to the skin.

20. The sunscreen or daily care composition according to claim 1, wherein the composition comprises (i) hexyl 2-[4-(diethylamino)-2-hydroxybenzoyl]benzoate (INCI diethylamino hydroxybenzoyl hexyl benzoate) and (ii) 1-(4-(1,1-dimethylethyl)phenyl)-3-(4-methoxyphenyl)propane-1,3-dione (INCI butyl methoxydibenzoylmethane) in a ratio of from 1:1 to 5:1.

* * * * *